United States Patent [19]
Thorne et al.

[11] Patent Number: 5,570,783
[45] Date of Patent: *Nov. 5, 1996

[54] APPARATUS AND METHODS FOR TRANSPORTING AND DISCARDING MEDICAL MATERIALS

[75] Inventors: Gale H. Thorne; David A. Robinson, both of Bountiful; Brad C. Robinson, North Salt Lake, all of Utah

[73] Assignee: Specialized Health Products, Inc., Bountiful, Utah

[*] Notice: The term of this patent shall not extend beyond the expiration date of Pat. No. 5,474,180.

[21] Appl. No.: 417,797

[22] Filed: Apr. 6, 1995

Related U.S. Application Data

[63] Continuation-in-part of Ser. No. 294,533, Aug. 23, 1994, Pat. No. 5,474,180, which is a continuation-in-part of Ser. No. 207,480, Mar. 7, 1994, abandoned.

[51] Int. Cl.$^6$ ..................................................... B65D 85/20
[52] U.S. Cl. ............................................. 206/366; 206/370
[58] Field of Search ..................................... 206/363–370, 206/438–443; 220/908–910

[56] References Cited

U.S. PATENT DOCUMENTS

| | | |
|---|---|---|
| 930,113 | 8/1909 | Adams. |
| 1,045,607 | 11/1912 | Payne. |
| 1,121,426 | 12/1914 | Walter ..................................... 229/154 |
| 1,580,104 | 4/1926 | Hasselmann. |
| 1,697,359 | 1/1929 | Huffman. |
| 1,820,804 | 8/1931 | Huffman. |
| 2,226,215 | 12/1940 | Borah ................................. 229/125.37 |
| 2,338,315 | 1/1944 | Borah ................................. 229/125.37 |
| 2,435,994 | 2/1948 | Zukerman ............................... 206/43 |
| 2,962,155 | 11/1960 | Rusciano ................................ 206/17.5 |
| 2,971,688 | 2/1961 | Akers ..................................... 229/38 |
| 2,990,059 | 6/1961 | Hitt ........................................ 206/63.2 |
| 3,080,087 | 3/1963 | Cloyd ..................................... 220/31 |
| 3,148,822 | 9/1964 | Yochum, Jr. ........................... 229/45 |
| 3,494,536 | 2/1970 | Henry ................................... 206/370 |
| 3,900,550 | 8/1975 | Oliver et al. .......................... 264/320 |
| 3,979,016 | 9/1976 | Frater .................................... 220/315 |
| 4,009,818 | 3/1977 | Rogers ................................. 229/23 R |
| 4,037,754 | 7/1977 | Wilhelmi et al. ...................... 220/254 |
| 4,040,419 | 8/1977 | Goldman .............................. 128/215 |
| 4,106,621 | 8/1978 | Sorenson ............................. 206/365 |

(List continued on next page.)

FOREIGN PATENT DOCUMENTS

| | | |
|---|---|---|
| 484294 | 5/1992 | European Pat. Off. . |
| WO89/01905 | 3/1989 | WIPO . |

OTHER PUBLICATIONS

Devon Industries Product Brochure, Published 1993.

*Primary Examiner*—Jimmy G. Foster
*Attorney, Agent, or Firm*—Gale H. Thorne; Paul S. Evans

[57] ABSTRACT

A container assembly for transport of new devices and for later disposal of sharps and other medical waste, the assembly comprising a secure closure for transport and tamper evidence upon its being opened for access to new devices is disclosed and claimed. The transport and disposal container assembly preferably has a container body with a device ingress and egress opening, a lid for use with multiple-sized container bodies and at least one apparatus which produces tamper evidence when accessing new devices stored for transport within the assembly. Evidence of tampering comprises at least one of (1) a collar which releasibly, but securely interconnects the container body and lid for transport of new devices, (2) a shrink wrap disposed over the entire container and (3) a seal over the container body opening. In one embodiment, the container assembly, when used for disposal, includes a lid having a self-closing biased flap and a cradle member and a safety guard disposed inside the assembly which restricts direct or line-of-sight access to sharps and medical waste previously deposited within the assembly. In addition a lid having a tube cutter and a lock which permanently restricts access to the assembly when the container is filled or retired from use is disclosed. Also, a unitary lid made by a single injection molding step is disclosed.

51 Claims, 22 Drawing Sheets

U.S. PATENT DOCUMENTS

| | | | |
|---|---|---|---|
| 4,121,755 | 10/1978 | Meseke et al. | 229/38 |
| 4,149,578 | 4/1979 | Hickley | 150/5 |
| 4,212,415 | 7/1980 | Neely | 222/231 |
| 4,270,536 | 6/1981 | Lemelson | 128/218 |
| 4,273,123 | 6/1981 | Lemelson | 128/218 |
| 4,315,592 | 2/1982 | Smith | 229/38 |
| 4,328,904 | 5/1982 | Iverson | 220/256 |
| 4,375,849 | 3/1983 | Hanifl | 206/366 |
| 4,452,358 | 6/1984 | Simpson | 206/366 |
| 4,520,926 | 6/1985 | Nelson | 206/366 |
| 4,576,281 | 3/1986 | Kirksey | 206/370 |
| 4,600,112 | 7/1986 | Shillington et al. | 215/274 |
| 4,679,700 | 7/1987 | Tharrington et al. | 220/337 |
| 4,722,472 | 2/1988 | Bruno | 229/128 |
| 4,733,778 | 3/1988 | Boeckmann et al. | 206/332 |
| 4,804,090 | 2/1989 | Schuh et al. | 206/366 |
| 4,809,850 | 3/1989 | Laible et al. | 206/366 |
| 4,816,307 | 3/1989 | Honeycutt | 428/34.1 |
| 4,826,073 | 5/1989 | Bruno | 229/128 |
| 4,840,272 | 6/1989 | Goldman | 206/365 |
| 4,848,569 | 7/1989 | Leishman | 206/365 |
| 4,874,103 | 10/1989 | Quisenberry et al. | |
| 4,890,733 | 1/1990 | Anderson | 206/365 |
| 4,900,500 | 2/1990 | Honeycutt | 264/263 |
| 4,903,832 | 2/1990 | Stewart | 206/366 |
| 4,930,631 | 6/1990 | Bruno | 206/366 |
| 4,936,449 | 6/1990 | Conrad et al. | 206/366 |
| 4,946,064 | 8/1990 | VanCucha | 220/355 |
| 4,969,554 | 11/1990 | Sawaya | 206/370 |
| 4,979,616 | 12/1990 | Clanton | 206/364 |
| 4,982,843 | 1/1991 | Jones | 206/366 |
| 5,054,618 | 10/1991 | Kim | 206/605 |
| 5,080,251 | 1/1992 | Noack | 220/335 |
| 5,103,997 | 4/1992 | Shillington et al. | 220/481 |
| 5,107,990 | 4/1992 | Wicherski et al. | 206/366 |
| 5,117,997 | 6/1992 | Fink | 220/23.86 |
| 5,183,180 | 2/1993 | Hawkins | 220/908 |
| 5,184,720 | 2/1993 | Packer et al. | 206/366 |
| 5,193,740 | 3/1993 | Newborough et al. | 206/370 |
| 5,269,457 | 12/1993 | de la Fuente | 206/366 |
| 5,271,500 | 12/1993 | Szacon | 206/366 |
| 5,494,158 | 2/1996 | Erickson | 206/366 |

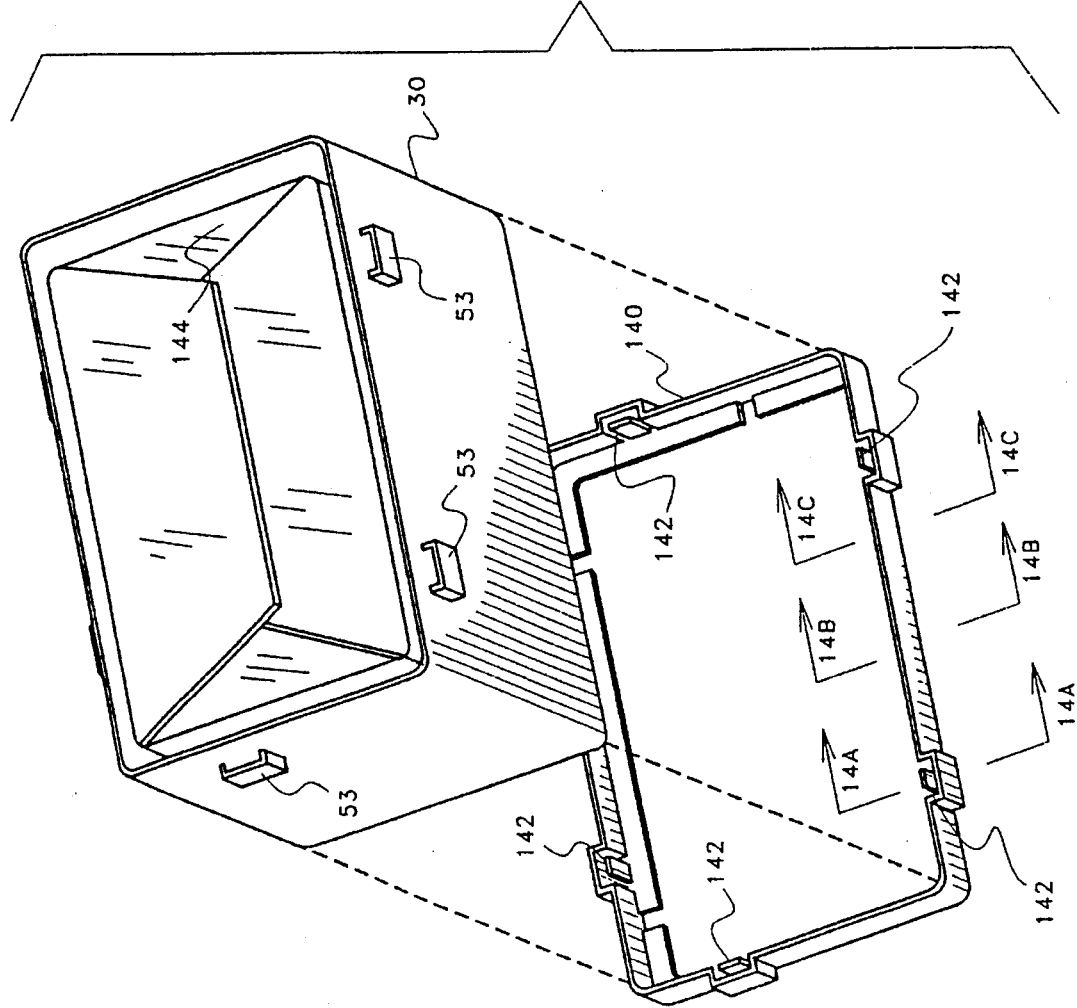

APPARATUS AND METHODS FOR TRANSPORTING AND DISCARDING MEDICAL MATERIALS

This patent application is a continuation-in-part of U.S. patent application Ser. No. 08/294,533 filed Aug. 23, 1994, U.S. Pat. No. 5,474,180, which is a continuation-in-part of another U.S. patent application Ser. No. 08/207,480, filed on Mar. 7, 1994, now abandoned, the disclosures of both applications are specifically incorporated herein.

BACKGROUND OF THE INVENTION

1. Field of the Invention

The present invention relates generally to container assemblies which are useful for both transport and disposal of sharp medical instruments and other medical materials and more specifically to container assemblies which provide evidence of tampering when opened after transport of new medical materials, to container assemblies which deny direct access through to sharps which have been previously deposited in the container assembly and to container assemblies which comprise apparatus for severing a tube to which a medical needle is attached to thereby deposit the needle and only a portion of the tube in the container assembly.

2. The Present State of the Art

The possibility of exposure to AIDS or other life-threatening diseases by medical personnel disposing of used sharp medical instruments has created a crucial need for an improved container that provides better protection against contracting potentially deadly diseases. The term "sharps" refers to sharp medical instruments such as syringes, scalpels, lances, and the like.

Sharps containers have been developed to facilitate the disposal of used medical instruments. Used instruments may be contaminated by bodily fluids of patients, or for other reasons may require sanitary disposal. However, the typical sharps container requires medical personnel to handle the sharp instrument during insertion into the container. For example, some sharps containers have two biased flaps through which sharps are horizontally inserted by pressing downward on the sharp while forcing it into the container. As the container fills, medical personnel run the risk of being stabbed by a previously inserted needle. As well, it is common for sharps containers to provide ready and direct access to previously deposited sharps through a container opening.

Additionally, improvements in the ability to transport unused sharps and to dispose of them in the same container would be desirable. New sharps are typically transported in one type of container and then disposed of in another container after use. Further, it is generally recognized by those skilled in transport and delivery of medical instruments that it is critically important to provide evidence of tampering for each user immediately prior to opening a container of new medical instruments. Also, it is desirable to provide for locking or sealing the lid of a container filled to a level at which it is ready for final disposal.

In some cases, in the handling of butterfly needles securely affixed to long tubes for example, it is desirable to cut the tube near the needle to deposit the needle into one container for one mode of disposal and the remaining tube into another container for another mode of disposal.

SUMMARY OF INVENTION

The present invention seeks to resolve a number of the problems which have been experienced in the prior art, as identified above. More specifically, the apparatus and methods within the scope of this invention constitute an important advance in the art of containers, as evidenced by the following objects and advantages realized by the invention over the prior art.

One object of the present invention is to preclude handling of items being disposed of by personnel during insertion into the container, thereby precluding contact with previously disposed sharps or other medical materials.

It is an important object to provide a convertible container which affords safe and secure transport of new medical equipment, such as new sharps, and later conversion to a sharps container.

It is an equally important object to provide evidence of tampering if the container is prematurely opened, by another, prior to steps by a bonafide user of removing new sharps and converting the container to a sharps container.

It is a consequential object to provide a safety guard which denies direct access, through the opening dedicated for deposition of used sharps, to items previously deposited within the container.

Yet another object of the present invention is to provide for interchangeable use of a lid with a plurality of container bodies dedicated to receipt of used sharps.

Another object of the present invention is to provide a self-closing flap over the container opening.

Additionally, it is an object of the present invention to provide a means for locking the lid of the container in a closed position to make it tamper resistant.

A further object of the present invention is to provide a means for removal and disposal of syringe needles.

As it is sometimes desirable to separate a needle securely affixed to a length of tubing such that the needle is stored in a sharps container and the robing is severed for later disposal in another container, it is an object to provide a robe cutter apparatus as a pan of the lid.

The container must also be disposable and made of nontoxic and incineratable materials, whereas the container may be incinerated and/or disposed of at a disposal site.

Additional objects and advantages of the invention will be apparent from the description which follows, or may be learned by the practice of the invention.

Briefly summarized, the foregoing objects are achieved by a container assembly which is utilized for both the transport of new sharps and the disposal of contaminated or used sharps.

The preferred embodiment comprises a lid and container body. The lid is designed to be interchangeable with a variety of different sized container bodies. The lid is also designed to be temporarily secured to the container body while transporting new medical instruments. When using the container for disposal purposes, the lid is preferably permanently secured to the container body.

When using the container for transporting new medical instruments, the lid is also securely affixed to the container body but is releasable in a manner which provides evidence of tampering when removed. A complement of tamper evidence producing mechanisms provide a plurality of tamper evidence producing choices including a collar which locks the lid in place upon the container body, a shrink wrap which encloses the entire container and a cover which encloses new medical instruments stored in the container body.

The opening of the lid is relatively restricted. While allowing for receipt of contaminated medical instruments, the lid opening substantially prevents removal of previously disposed instruments in the associated container. The lid includes an area for placement of a contaminated article wherein a person may then deposit the article into the container body without touching the article presently being disposed of as well as previously disposed articles by activity of a single hand. Moreover, the lid prevents further handling of used items by medical personnel subsequent to disposal.

Further, one embodiment of the container comprises a safety guard which denies direct (straight line) access to items deposited within the container through the lid opening. In some applications, a tube cutter may be incorporated into the lid to permit a needle, while resident in the container, to be separated from tubing to which it had been previously secured.

Non-medical items may also be stored, transported and disposed of through the use of the inventive lid and container assembly. For example, batteries, industrial items, chemical items, cosmetics and computer software may be transported in a container incorporating the present invention and then disposed of in the same container. Household items such as chlorine bleach, lye, soap, phosphates, ammonia, vinegar and alcohol may also be transported and then disposed of in the same container.

When used with medical or chemical products, the container assembly may also contain an absorbent pad and chemical agents for neutralizing the items. In addition, the inventive container assembly may be used for transport and storage of agricultural items and automotive parts. Soiled automotive parts may later be safely disposed of in the same container. Other uses for the container include transport and disposal of environmentally unsafe products such as coal and oil.

These and other features of the present invention can be best understood from the following specification and drawings, of which the following is a brief description.

BRIEF DESCRIPTION OF DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through use of the accompanying drawings in which:

FIG. 14 is an exploded perspective of the container body and lid securing collar seen in FIG. 13, with some parts of the collar removed for clarity of presentation.

DETAILED DESCRIPTION OF THE PREFERRED EMBODIMENT

Figure 1:
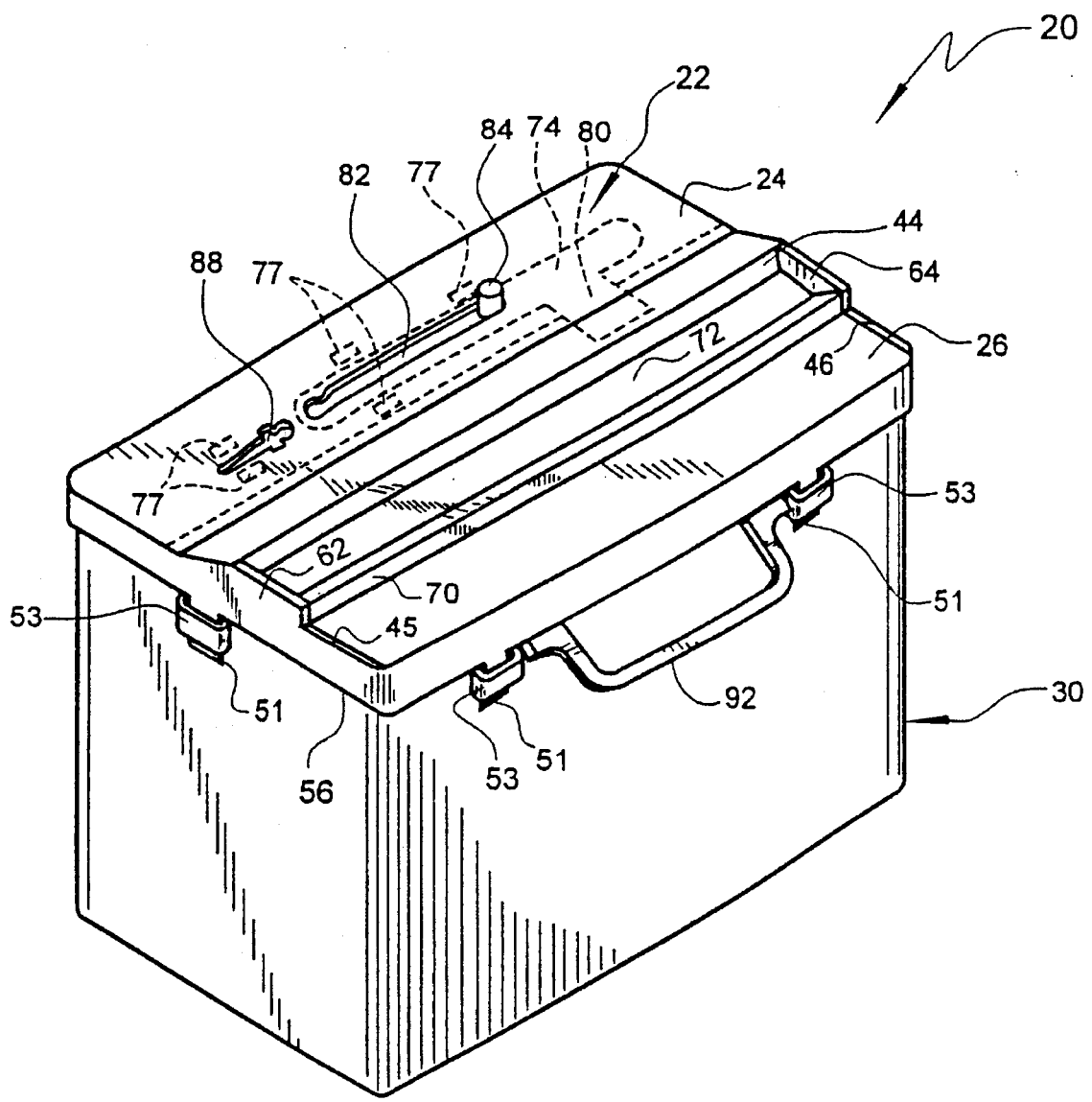
FIG. 1 is a perspective showing the container assembly in a closed position.

Reference is now made to the drawings, wherein like numerals are used to denote like elements throughout. In FIGS. 1–8, the container assembly of the present invention, generally designated 20, comprises a lid body 22, a self-closing biased flap 26, an opening 28, and a container body 30.

In those cases where items in FIGS. 9–25B are similar, but not exactly like items in FIGS. 1–8, numbers with primes are used to signify a difference. For example, a different lid body may be signified by 22' or 22" instead of lid body 22 as seen in FIGS. 1.

Figure 5:
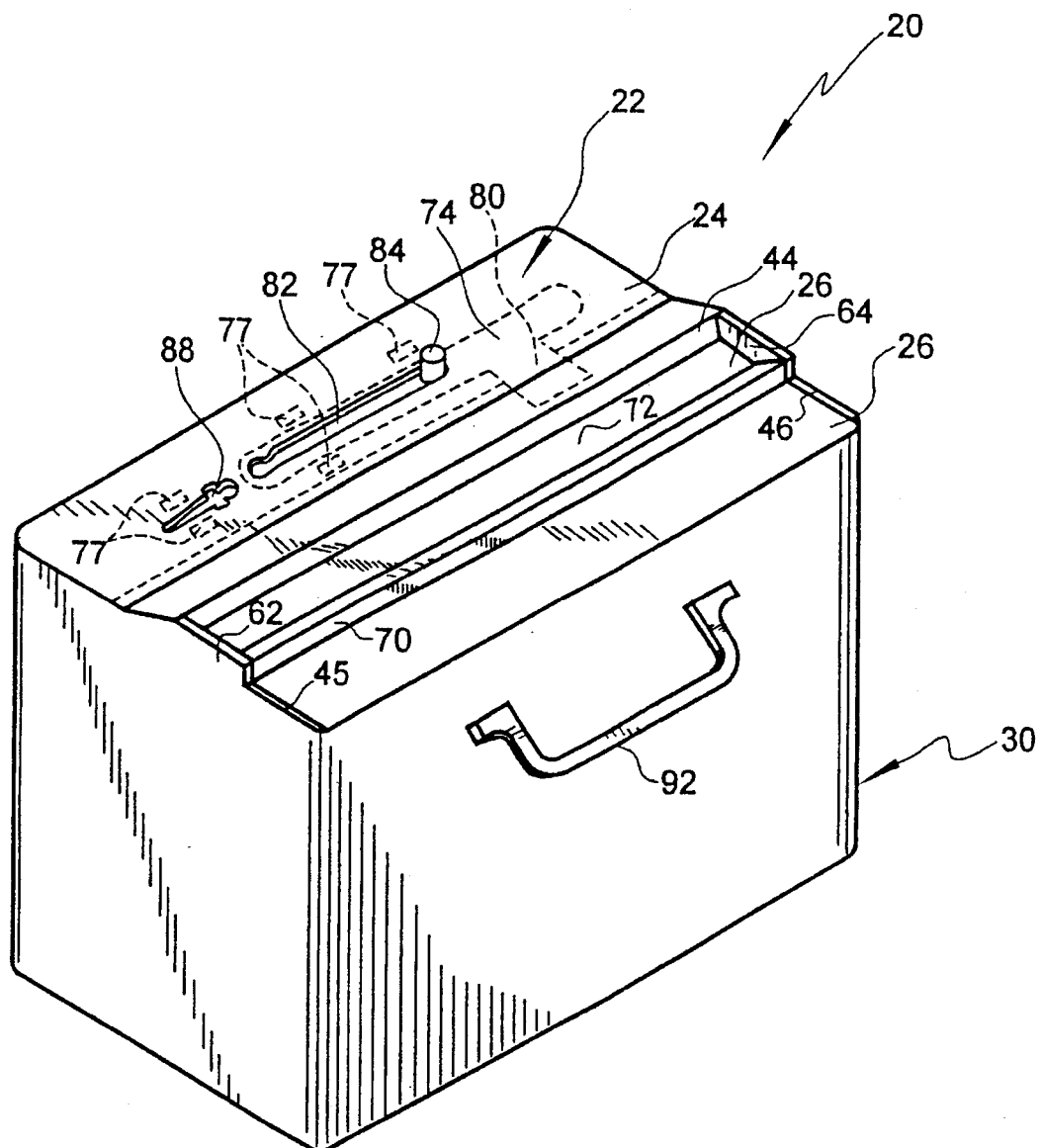
FIG. 5 is a perspective showing the lid formed as part of the container assembly.
Figure 6:
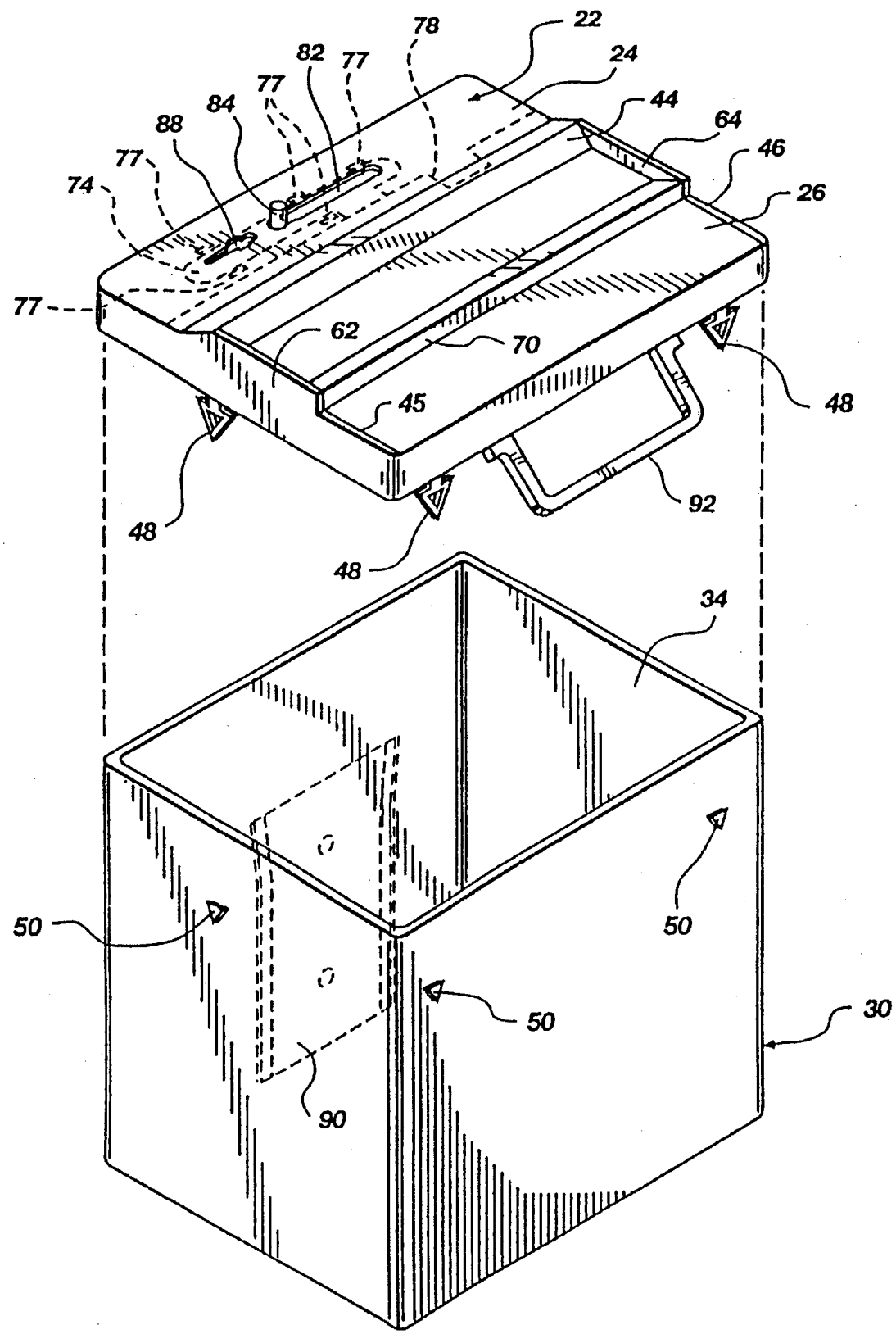
FIG. 6 is a perspective showing an alternative means for securing the lid to the container by means of arrow tabs.
Figure 7:
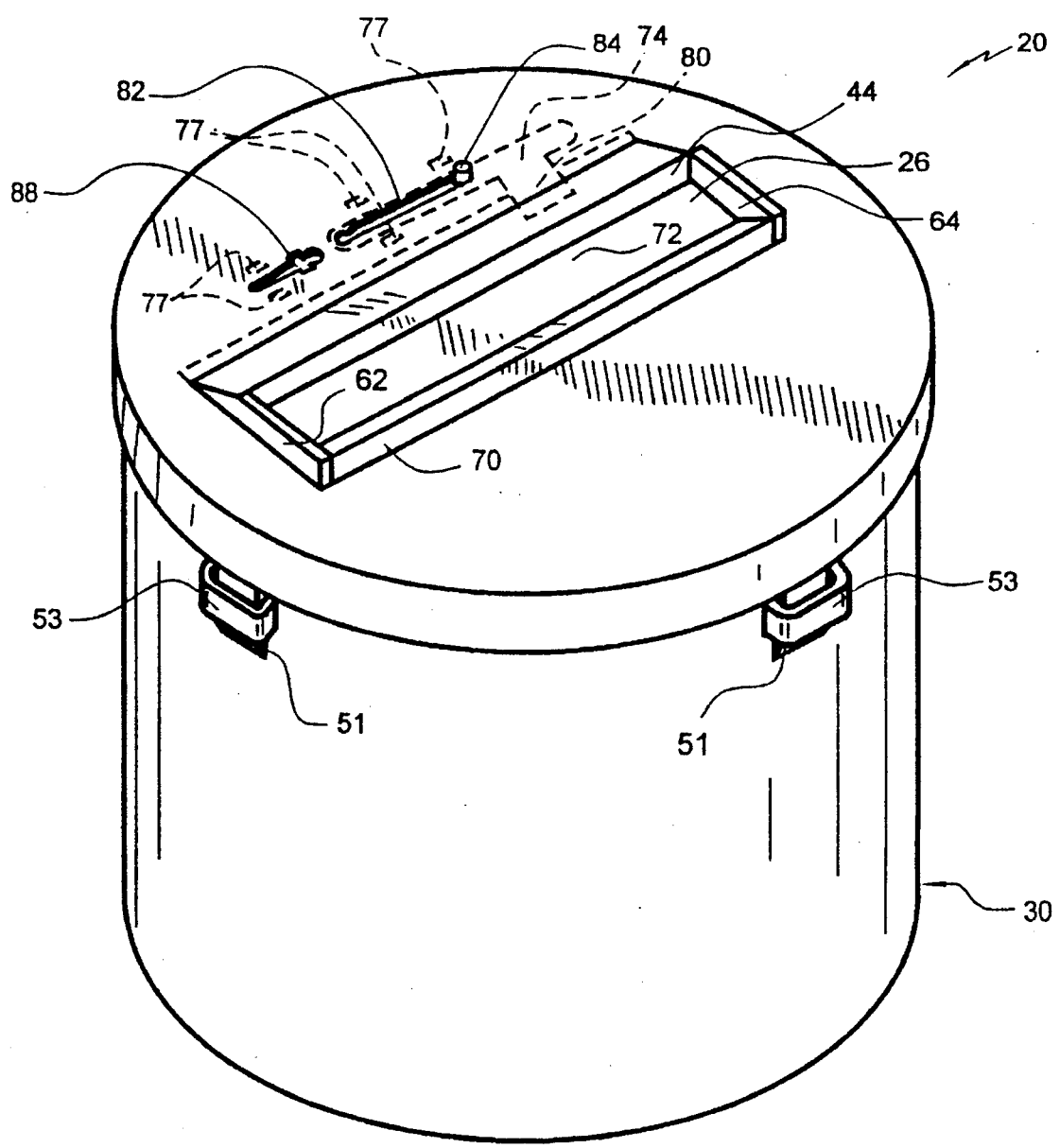
FIG. 7 is a perspective showing a cylindrical container assembly.
Figure 8:
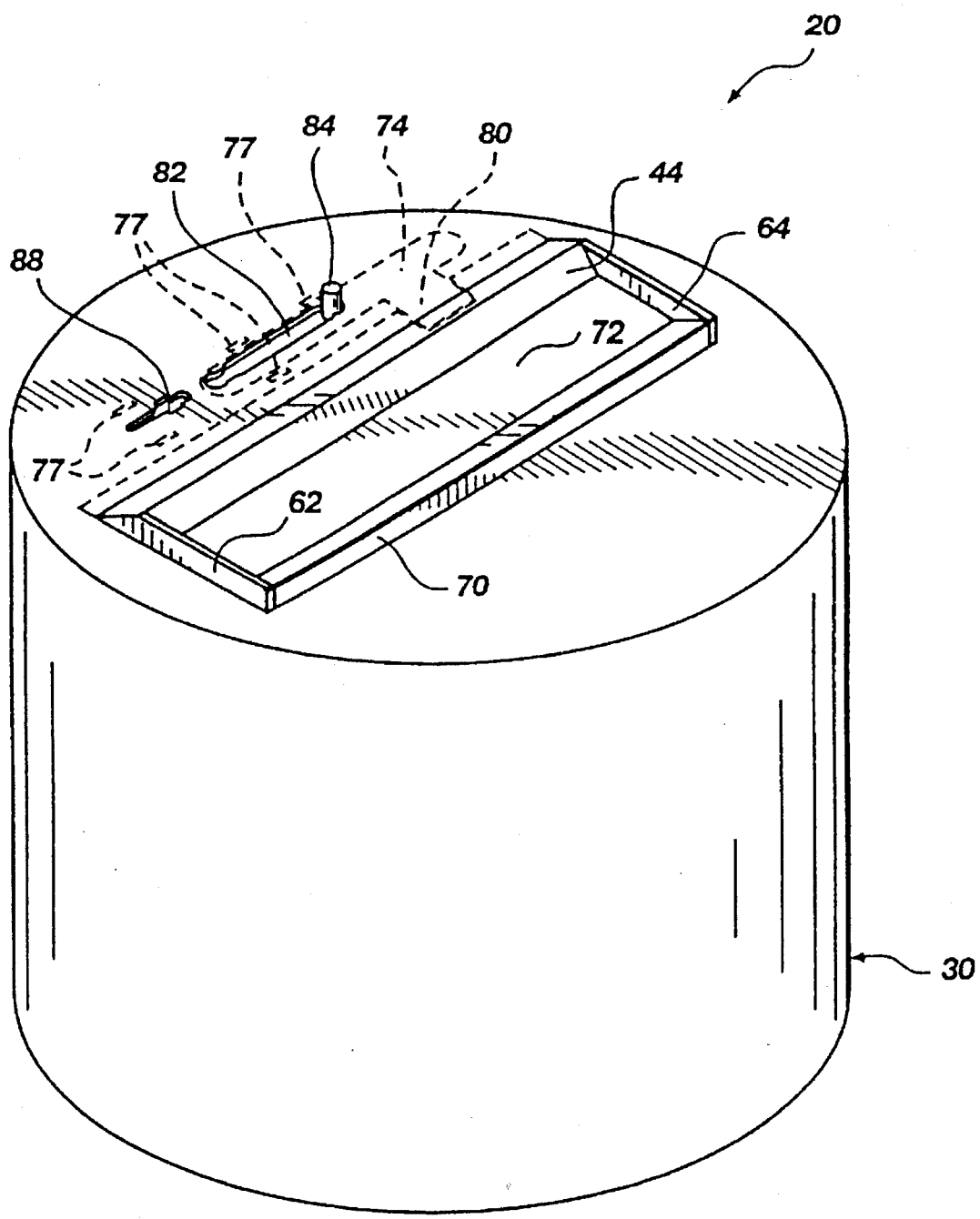
FIG. 8 is a perspective showing the lid formed as part of the cylindrical container body.

The container body 30 defines a volume 32 and includes an opening 34. Although FIGS. 1–6 illustrate a rectangularly shaped volume 32, one skilled in the art will recognize that many other shapes fall within the purview of this invention. For example, the container assembly may be square, spherical or cylindrical in shape as shown in FIGS. 7 and 8. Of course, manufacturing concerns are important in determining the shape of the volume 32. In the preferred embodiment, the lid body 22 is separate from the container body 30. The lid body 22 is adapted to be used with a plurality of container bodies 30. This design feature facilitates the manufacturing ease in which a variety of multiple-sized containers are produced for use with a one-size-fits-all container lid. However, the lid body 22 may also be formed as part of the container body 30 as shown in FIGS. 5 and 8. Each of these elements, as well as many others, will be discussed in greater detail hereafter.

The lid 22 and container body 30 are preferably constructed of a semi-rigid plastic or similar material which is lightweight, non-toxic, incineratable, inexpensive, easily manufactured, and sturdy. Size considerations may dictate that the container body 30 further comprises ribs to enhance structural integrity.

The biased flap 26 includes a first end 66 and a second end 68 wherein the biasing feature is accomplished by a living hinge 38 at the first end 66. A living hinge is herein defined to be a hinge formed of material having memory, such that when the material at the hinge is forcibly bent, the material returns to its original position at the hinge. The hinged material may be notched along the living hinge. The biasing may also be accomplished by a spring interposed between the biased flap 26 and the container body 30.

The container assembly 20 also comprises a cradling means for insertion of medical instruments and waste into the container body 30 through the opening 28, wherein the cradling means has a floor 72 which in one embodiment is disposed on the biased flap 26. In another embodiment, floor 72 is in contact with, but separate from biased flap 26. The cradling means is defined by an area surrounded by enclosure walls. A first enclosure wall 70 extends outwardly from the container body 30. The biased flap 26 has a first side 45 and a second side 46, wherein the first enclosure wall 70 extends from the first side 45 to the second side 46 of the biased flap 26 and is located between the first end 66 and the second end 68 of the biased flap 26. The second enclosure wall is defined by a combination of enclosure walls 44, 62, and 64. When floor 72 is disposed at a position inferior to enclosure walls 62 and 64, vertical sides of container body 30 form the enclosing walls. The second enclosure wall extends outwardly on the container body opening 34 and is defined by the perimeter of the container body opening 34 abutting the second end 68 of the biased flap 26 and the first side 45 and second side 46 of the biased flap 26 between the first enclosure wall 70 and the second end 68 of the biased flap 26, such that a cradling means floor 72 is defined by the area enclosed by the first and second enclosure walls. One skilled in the art will recognize that the enclosure walls may be constituted in a number of combinations of securement to the lid body 22 or container body 30. For example, enclosure wall 62 and enclosure wall 64 may be formed with first enclosure wall 70 on the biased flap 26. Alternatively, first enclosure wall 70, enclosure wall 62, and enclosure wall 64 may be formed as part of enclosure wall 44 on the container body 30. The cradling means may also comprise a recessed area in the biased flap 26 or be a recessed area juxtaposing biased flap 26. For example, the biased flap 26 may step inwardly such that the sides of the container body 30 act as enclosure walls, as earlier stipulated.

The container assembly also comprises a stopping means for maintaining the biased flap 26 in a closed position. Preferably, the stopping means comprises a second flap 24 affixed to the container body 30 at the opening 34 and extending towards the biased flap 26 such that the second flap 24 overlies a portion 36 of the biased flap 26. The biased flap 26 is biased against the second flap 24 by use of living hinge 38. In this manner, the opening 28 is normally closed. In this embodiment, the second flap 24 also includes a first and second end 40 and 42, respectively. The second end 42 of the second flap 24 includes an enclosure wall 44 protruding in a direction normal to the second flap 24. The stopping means may also comprise one or more tabs positioned at the container opening 34 and overlying a portion of the second end 68, first side 45, or second side 46 of the biased flap 26.

The lid body 22 is attached to the container body 30 by an attaching or securing means. In the preferred embodiment, the attaching means comprises a plurality of tabs 47 located on the perimeter of the lid body 22. Each tab 47 includes a distal end at which is disposed a protruding edge 51 for engagement with a corresponding female slot 53 located on the container. Once the tab 47 is fully inserted through the female slot 53, the protruding edge 51 locks the tabs in place. Alternatively, hinged pull tabs hingedly secured to the lid may be utilized, as shown in FIG. 6. In this embodiment, each pull tab includes a female end 48 of an arrow lock for engagement with a corresponding male end 50 located on the container body 30. One skilled in the art will recognize that these methods serve as attaching or securing means, although other methods may be used which are equivalent and thus fall within the scope of this invention. For example, the securing means may comprise a tongue and groove configuration or other locking tab configurations typically found in lid and container assemblies. The attaching means may be continuous or intermittent around the perimeter of the container opening 34 and lid body 22.

In the preferred embodiment, the tabs 47 and slots 53 are not positioned symmetrically about the perimeter of the lid 22 so that the lid 22 can be rotated one-hundred and eighty degrees to avoid permanent securement during shipment of new medical instruments. Once the new medical instruments are removed, the lid 22 is then oriented for engagement of the tabs 47 into the corresponding slots 53 for permanent securement while using the container 30 for disposal purposes. Alternative securing means would similarly be misaligned for temporary and later permanent securement.

Figure 2:
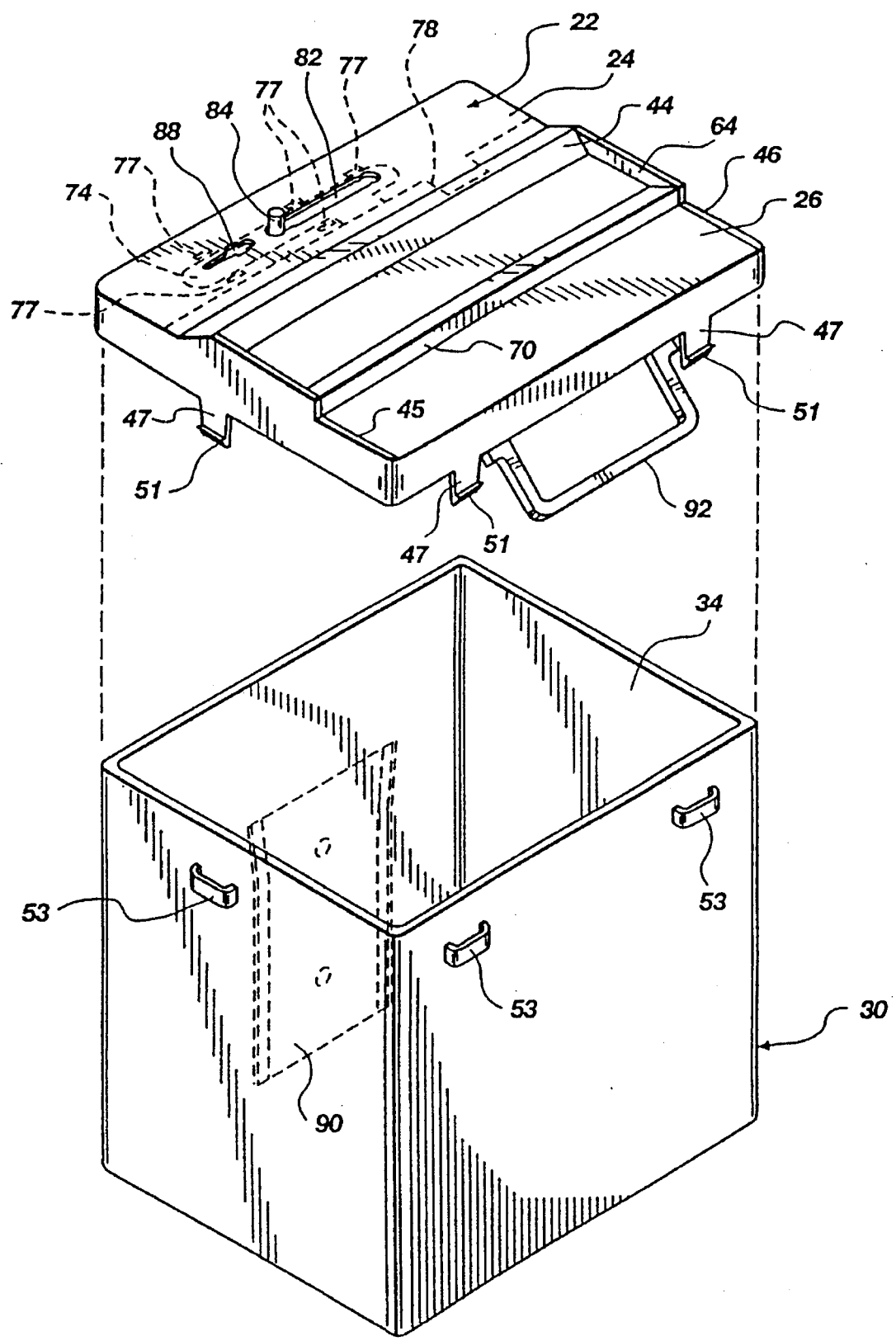
FIG. 2 is a perspective showing the lid separate from the container.
Figure 3:
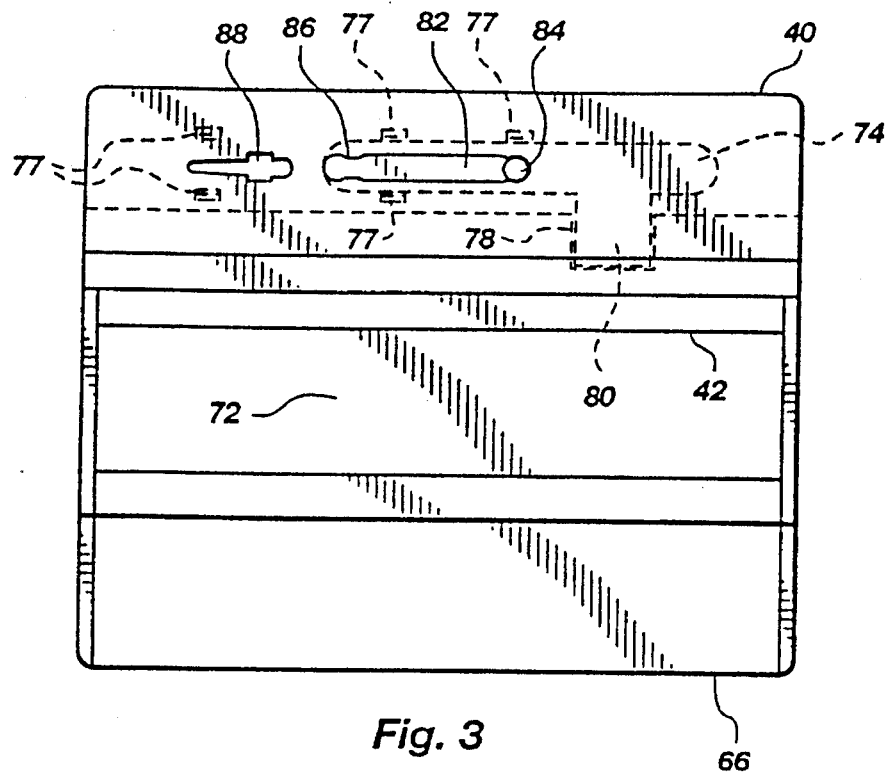
FIG. 3 is a top view of the container assembly in a closed position.
Figure 4:
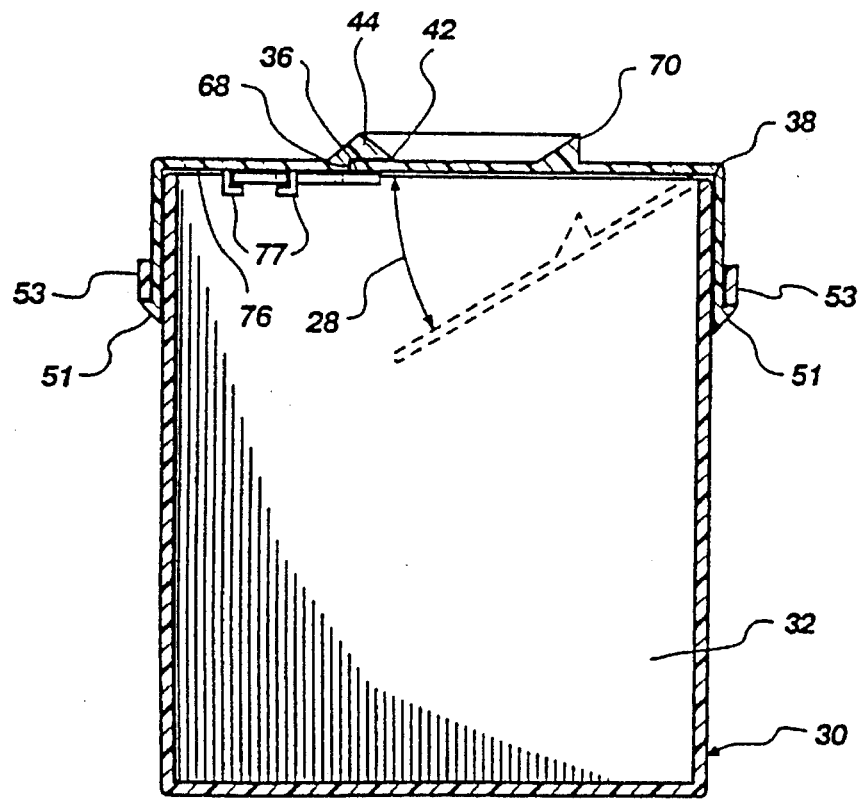
FIG. 4 is a cross-sectional view of the container assembly.

The container assembly 20 further comprises a means for locking the biased flap 26 in a closed position. In a preferred embodiment the locking means comprises a plate 74 slidably mounted to the underside 76 of the second flap 24. The plate 74 slides along tracks 77. The second end 68 of biased flap 26 includes a notch 78 which is configured to match the outline of a tab 80 extending outwardly from plate 74. The profile of the tab 80 is offset and therefore dose not contact notch 78 when plate 74 is in the open position so that the biased flap 26 may be freely depressed. The closed position is defined by positioning plate 74 such that the tab 80 is located adjacent to the notch 78 or at least covering a portion of end 68 of biased flap 26, thereby preventing depression of the biased flap 26, as shown in FIG. 2 (and also in FIG. 19). The second flap 24 also includes a slit 82 for slidable translation of a knob 84 attached to the plate 74 for positioning in an open, closed, or permanently closed or locked position. The permanently closed or locked position is defined by the knob 84 extended past a necked section 86 in the slit 82 of slightly smaller width than the knob 84.

Additionally, a strip of adhesive tape may be used as a method of sealing the first and second flaps 26 and 24, respectively, together.

Container assembly 20 further comprises a means for extracting needles from a syringe. In the preferred embodiment, a tapered opening 88 located on the second flap 24 is used for extracting needles from a syringe. The needle is removed from the syringe by slidably engaging the needle base in the narrowest portion of the tapered opening 88 allowed and then twisting the syringe such that the threaded needle base dislodges from the syringe and falls into the volume 32. The means for extracting needles may also comprise multiple-sized openings, either separate or in series, which correspond to the geometry of the base of the needle such that when the needle base is inserted through the opening, the sides of the opening lockably fix the needle base for removal of the needle and insertion into the container assembly 20.

Container assembly 20 is also adapted to be mounted to a wall surface by means of a bracket 90 which is attached to the container body 30 and a corresponding adapter rigidly secured to the wall surface. For example, this adaptation of container assembly 20 is advantageous in a hospital setting whereby a number of medical personnel may utilize the invention in a convenient and centralized locale.

Container assembly 20 is used for transporting and disposing of medical instruments as described hereafter. When container assembly 20 is used for transporting new medical instruments, the new instruments (likely disposed in a separate package) are placed inside the container volume 32 with the lid 22 temporarily secured by orienting the tabs 47 and slots 53 in the misaligned position. When the container assembly 20 is used for disposal of used medical instruments, the lid 22 is permanently secured to the container 30 by orienting the tabs 47 and corresponding slots 53 in the aligned position such that the tabs 47 slide through the slots 53 and the protruding edges 51 lock the tabs 47 in place. The medical instruments desired to be disposed of are inserted into the container assembly 20 by placing the instruments on the floor 72 of the cradling means defined by the enclosure walls, such as walls 44, 62,64 and first enclosure wall 70, and then pressing downward on the area between floor 72 of the cradling means and living hinge 38, thereby causing the instruments to fall inside the volume 32 without contact of soiled or contaminated instruments by the hand of the disposer. Once the instruments are deposited into container 20, the danger of one or more instruments accidentally falling out or injuring someone is virtually eliminated. When container 20 is filled to a predetermined level (preferably a level with is less than 75% of container capacity), lid 22 body of the container assembly 20 is then locked by sliding the knob 84 into the permanently locked position prior to transporting. A handle 92 attached to the container assembly 20 further facilitates its transportability.

Figure 9:
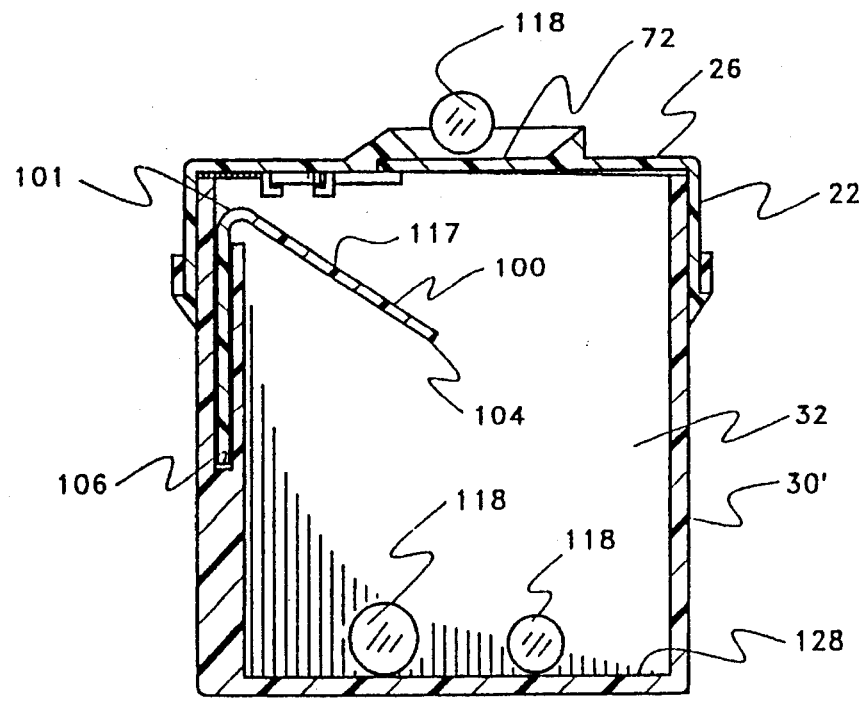
FIG. 9 is a cross-sectional view of a container assembly, similar to the container assembly seen in FIG. 4, wherein a safety guard is disposed below a closed lid.
Figure 10:
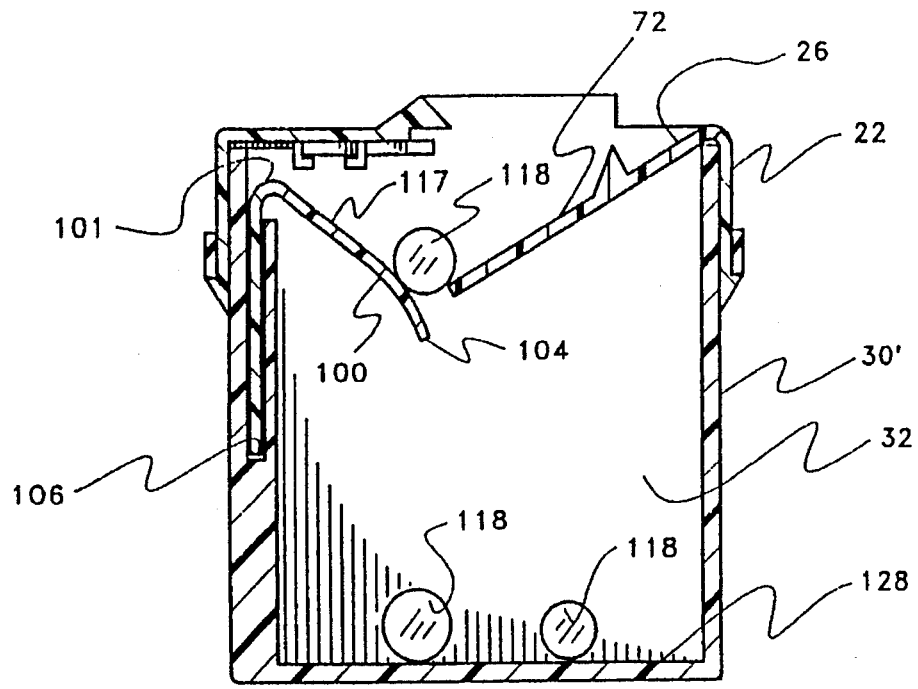
FIG. 10 is a cross-sectional view of the container assembly of FIG. 9, with the lid disposed in an open position.

Even though the danger of instruments accidentally falling out or injuring someone are virtually eliminated by the self-closing operation of living hinge 38, it may be tempting to an unwary user to retrieve an item previously deposited in volume 32. Reference is now made to FIGS. 9–12 wherein a novel safety guard is disclosed. As seen in FIGS. 9 and 10, a safety guard 100 is disposed to deny direct (straight line or line-of-sight) access through opening 28.

Figure 12:
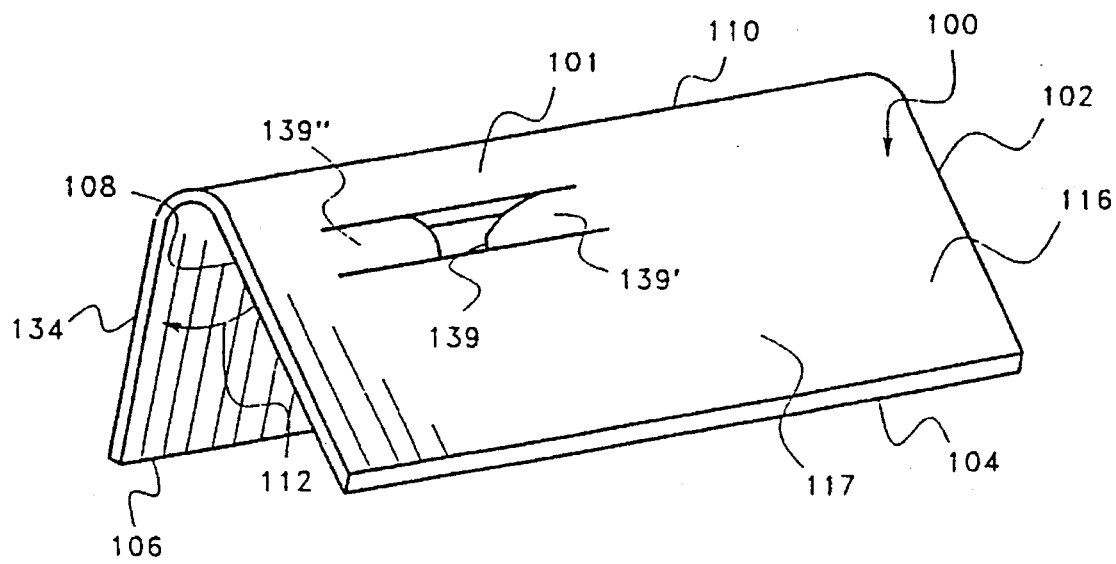
FIG. 12 is a perspective of a safety guard.

While safety guard 100 may be made in many forms as known and understood by one who is skilled in the art, the preferred embodiment of the safety guard should be inexpensive to make and easily installed into container assembly 20. As seen in FIG. 12, the presently preferred embodiment of safety guard 100 is made from a single sheet of material. The appropriate material may be plastic or a medium thickness grade of cardboard. If cardboard is used, it is preferably comprises a laminated plastic cover.

Guard 100 is formed by selecting a preferably rectangular sheet 101 of appropriate material which is cut to a size having dimensions which are defined hereafter. As seen in FIG. 12, sheet 101 comprises a plurality of edges, 102, 104, 106 and 108. Sheet 101 is bent or folded along a line 110 which is parallel with adjacent edges 104 and 106 of sheet 101. In this manner an angle 112 is formed between two preferably parallel juxtaposed sides 114 and 116. Sides 114 and 116 are disposed, one relative to the other, such that angle 112 is acute, preferably in the range of 70° to 80°, although other angles may usefully perform the function. One who is skilled in the art would understand the size of angle 112 is dependent upon dimensions and position of opening 28 and biased flap 26 relative to the dimensions and position of side 116.

The length of each edge 104 and 106 should be long enough to deny direct (line-of-sight) access to sharps and other items, generally designated 118, which are deposited within container volume 32. Similarly, that portion 117 of safety guard 100 which is disposed between 110 and edge 104 should be wide enough to deny direct access to items 118 deposited within container volume 32.

Figure 11:
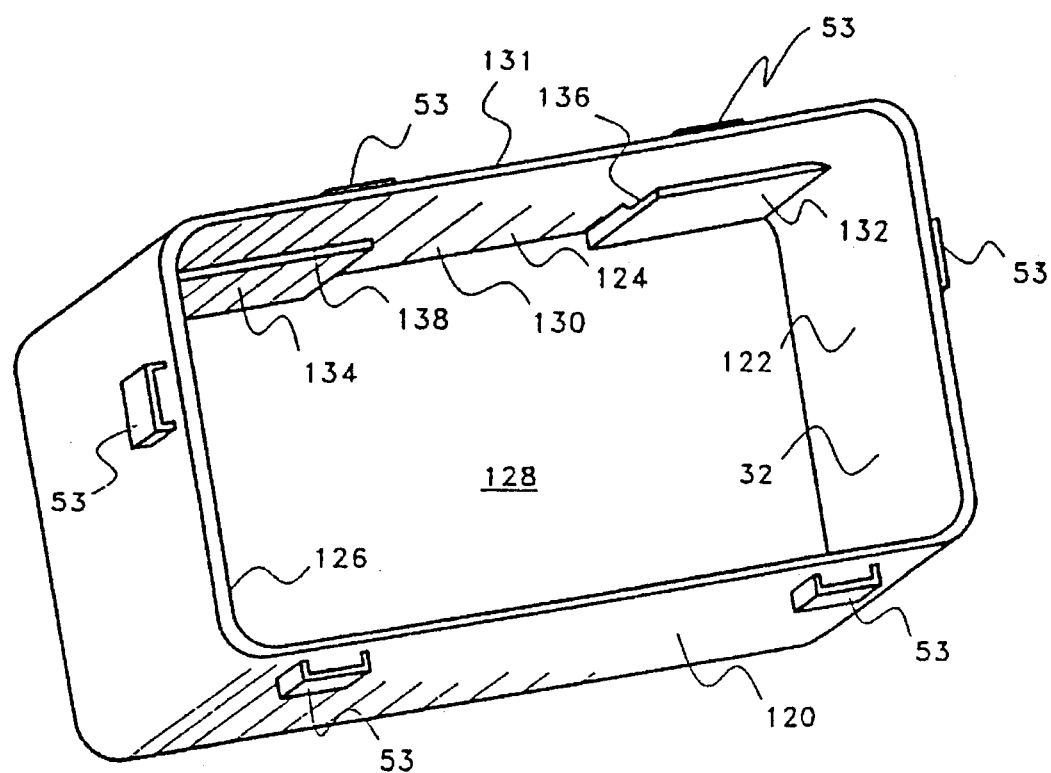
FIG. 11 is a perspective of a container body comprising safety guard slots for trapped attachment of the safety guard.

Referring now to FIG. 11, a container body 30' (which is similar to container body 30) is seen to comprise a front or label side, a first lateral side 122, a back side 124, a second lateral side 126 and a bottom 128. Also similar to container body 30, body 30' comprises a plurality of slots 53. Back side 124 comprises an inner surface 130 and a top edge 131 which is continuous about the top of container body 30' to form a rim therefore. Preferably integrally molded as part of the structure of back side 124 are a pair of plates 132 and 134. Each plate 132 and 134 is separated superiorly from back side 124 to form a slot 136 and 138, respectively.

Each slot 136 and 138 is sufficiently deep to permit that portion of safety guard 100 between edge 106 and line 101 to be fully disposed therein. Further, that portion of safety guard 100 which is disposed between edge 106 and line 101 is sufficiently wide to be securely trapped within each slot 136 and 138 when a container lid (such as container lid 22) is secured to container body 30'.

Function of safety guard 100 is best understood by reference to FIGS. 9 and 10. As seen in FIG. 9, a sharp or other item 118 destined for deposit within volume 32 is disposed on safety cradle floor 72. Biased flap 26 is then depressed into volume 32 causing item 118 to fall against portion 117 of safety guard 100. As best seen in FIG. 10, while portion 117 comprises sufficient turgor and spring along line 101 to maintain a normal effectively unbending state, when unburdened (as seen in FIG. 9), added weight of item 118 causes guard 100 to "give", thereby permitting item 118 to separate from floor 72 and ultimately fall toward bottom 128 within volume 32.

Safety guard 100 is preferably opaque, but may, if desired, be translucent or even transparent. It should be obvious to one who is skilled in the art that a relatively light weight sheet, such as the weight of plastic sheets used for overhead transparencies is preferred, although any sheet material which releasably permits each item 118 to be individually deposited into volume 32 may be used. However, physical characteristics of such a sheet should not deteriorate under use.

To provide a pathway for depositing needles and other materials through opening 88, an "H" cut 139 may be made in safety guard 100 at a site which is inferiorly disposed to opening 88. The form of "H" cut 139 provides a pair of leaves 139' and 139" which relax to provide a facile needle pathway.

Figure 13:
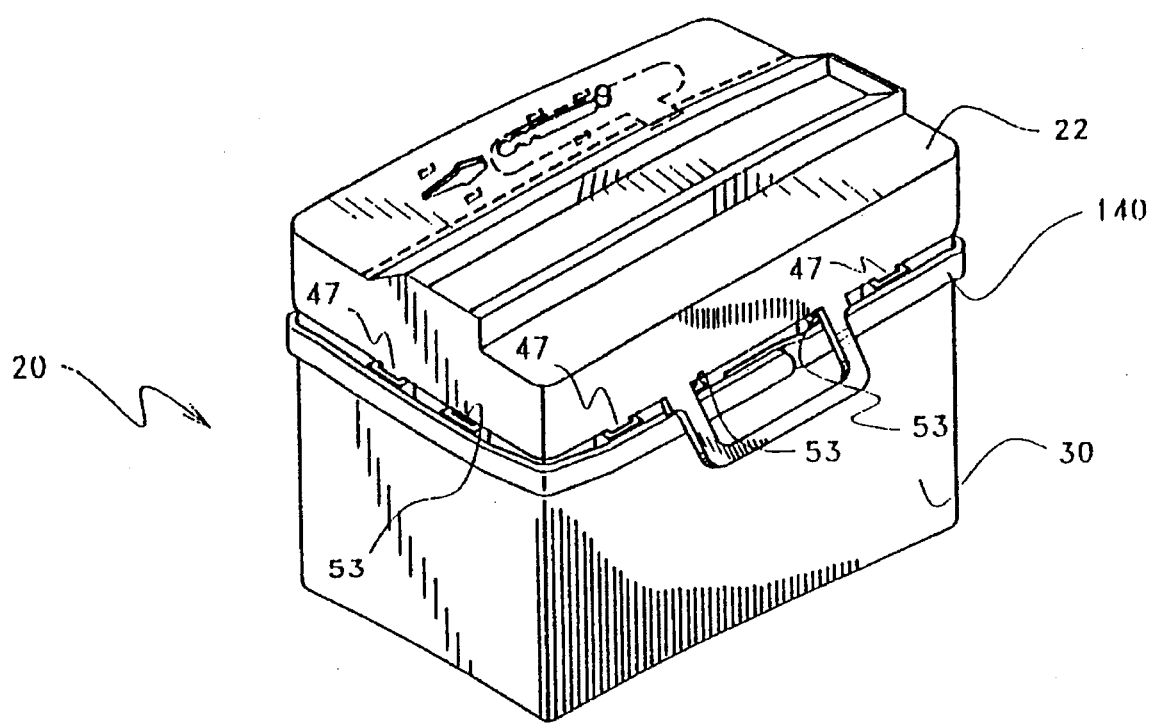
FIG. 13 is a perspective of a container assembly having a lid closed and secured by a collar, with some parts removed for clarity of presentation, the collar comprising parts which provide evidence of tampering when the collar is wholly or partially separated from the container assembly to release the lid for subsequent access to container contents.
Figure 15:
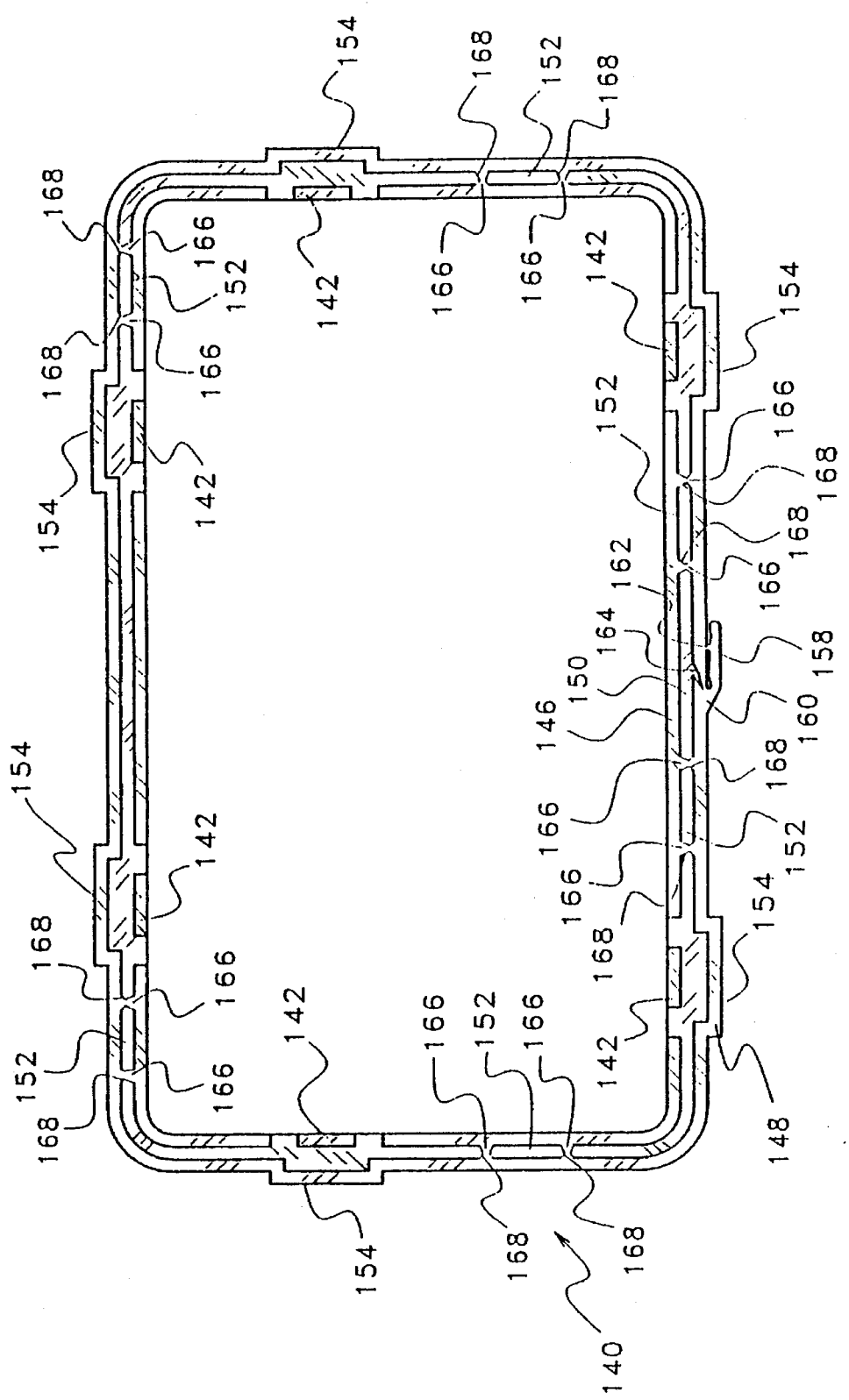
FIG. 15 is a top elevation of the collar seen in FIG. 14.

As transport of medical material comprises important issues such as protection from and detection of tampering, reference in now made to FIGS. 13–17 wherein the scope of the invention is seen to include a plurality of methods and apparatus which provide evidence of tampering upon opening container assembly 20 for access to new medical devices transported therein. In FIG. 13, a collar 140 is seen disposed about that portion of a lid and container assembly 20. Note that lid body 22 is disposed upon container body 30 in such a manner which no tab 47 is locked into a slot 53. However, collar 140 securely affixes lid body 22 to container body 30 for safe transport.

As seen in FIG. 14, a preferred embodiment of collar 140 is made to engage container body 30 by insertion of container body 30 into collar 140 such that a pattern of tabs 142 are selectively introduced into a similar pattern of previously described slots 53. After introduction of a package or assortment 144 of medical or other sensitive materials for transport in assembly 20, a container lid 22 is attached as disclosed hereafter.

Figure 14C:
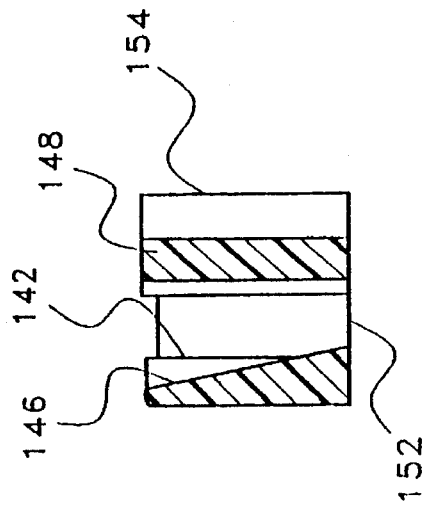
FIGS. 14A, 14B and 14C are sections of the collar seen in FIG. 14, respectively taken along lines 14A—14A, 14B—14B and 14C—14C.
Figure 14B:
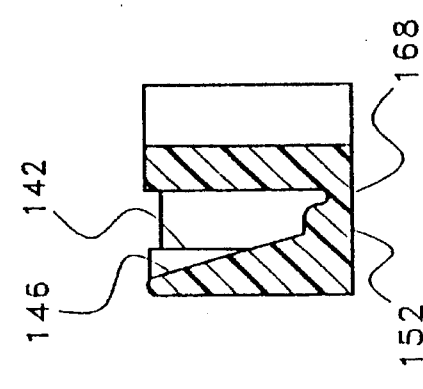
Figure 14A:
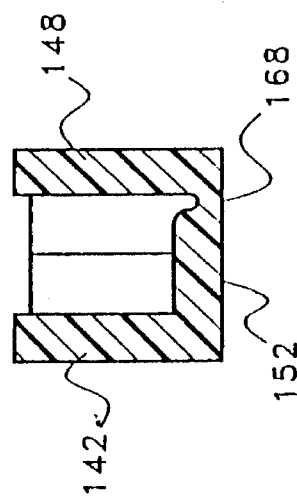

In combination, FIGS. 14, 14A–C and 15, show the form of collar 140. Collar 140 is generally comprises a "U" shaped channel, comprising an inner wall 146, an outer wall 148 and a base member 150. The general form of collar 140 is seen in FIG. 14B. Variations from the general form are seen in FIGS. 14A and 14C. FIG. 14A is exemplary of a portion of collar 140 which is juxtaposed to slot 53. FIG. 14C is illustrative of the form of collar 140 at a slot which is meant to capture a tab 47. Note that collar 140 is continuous along outer wall 148 and, in combination, along pans of inner wall 146 and base member 150.

In addition to the "U" elements, collar 140 comprises tabs 142 (previously mentioned) and slots 152 disposed to capture and lock each container lid 22 tab 47. At each site 154 where a tab 142 engages a slot 53, outer wall 148 is disposed outwardly from tab 142 to permit a slot 53 structure to reside therein. By this means, base member 150 provides a firm stop for collar 140 against each slot 53 structure.

Disposed at a relatively protected, but readily accessed site along the periphery of outer wall 148 is a break-away pull tab 158. In combination, pull tab 158 and outer wall 148 comprise a firm, contiguous attachment at a site 160 and preferably at least one detachable connection 162. Detachable connection 162 is preferably frangible. In addition, a thinned part 164 of outer wall 148 permits frangible breaking of wall 148 upon an outward pull of tab 158.

Juxtaposed on each end of slot 142 is a cross member 166 which provides a supporting tie between inner wall 146 and outer wall 148. At junctions, generally denoted 168, between base member 150 and outer wall 148, connecting members are also thinned to permit frangible separation. In this manner, by pulling on tab 158, outer wall 148 may be stripped from collar 140, thereby freeing each tab 47 and subsequently releasing lid 22 for removal from container base 30. Thus, access is provided to volume 32 and items 144 contained therein. Also, in this manner, tamper evidence is provided by change in form and appearance of collar 140 to provide a release of tabs 47.

Figure 16:
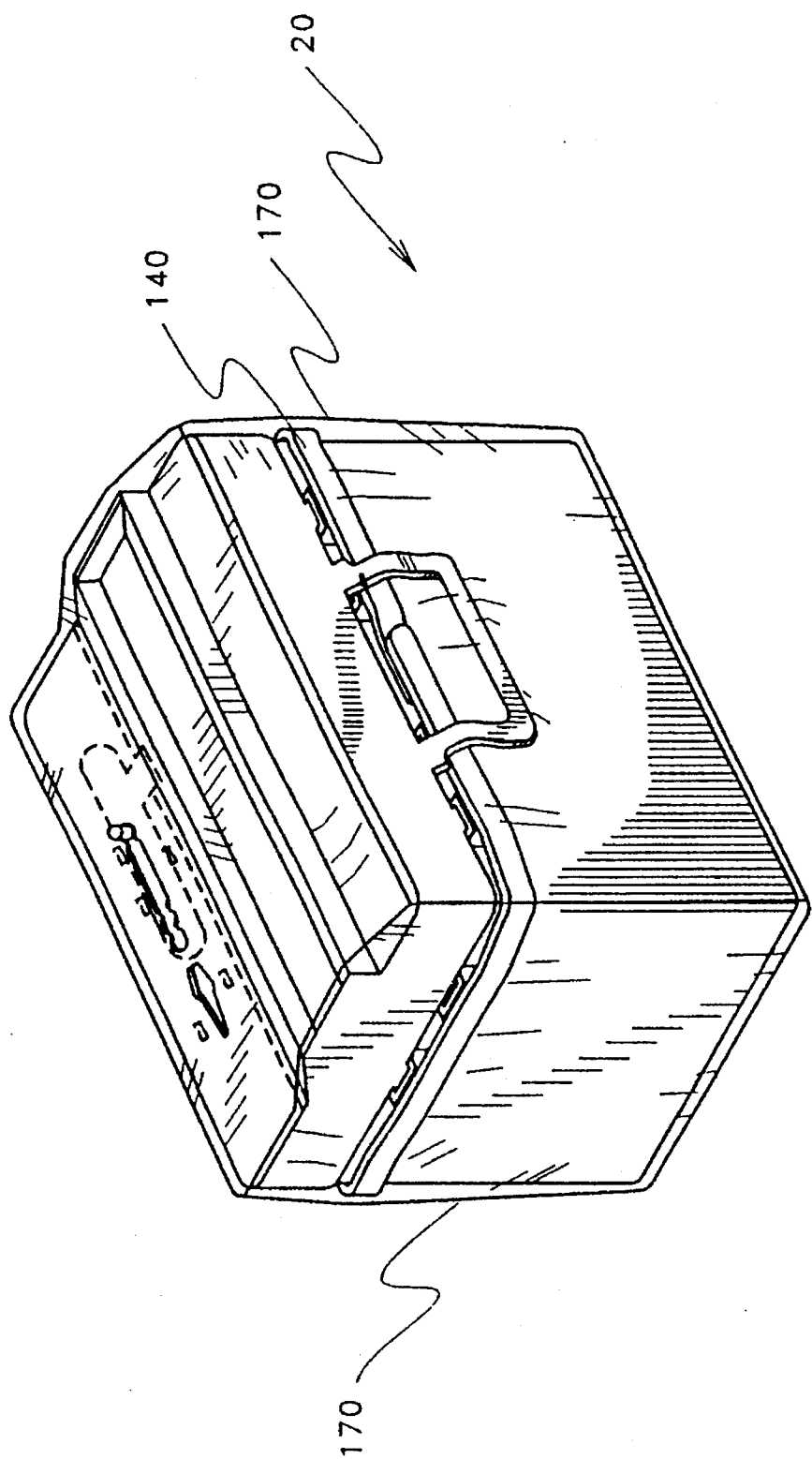
FIG. 16 is a perspective of a shrink wrapped container assembly.
Figure 17:
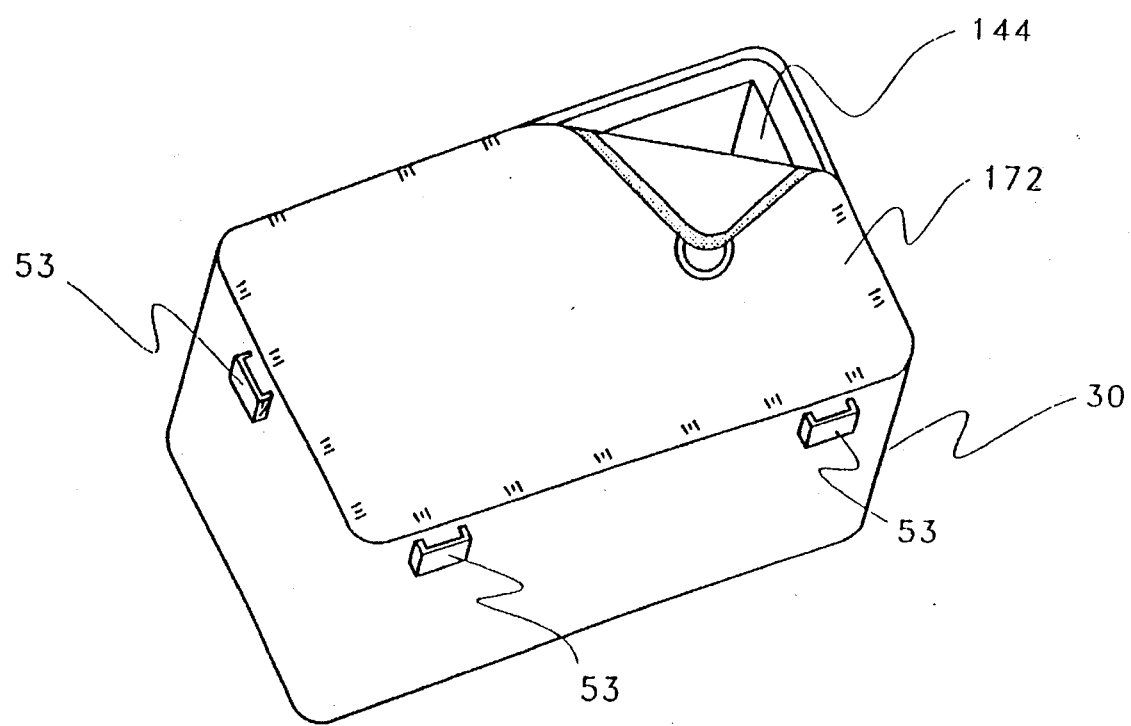
FIG. 17 is a perspective of a container body comprising a contents enclosing seal which provides evidence of tampering when partially or completely removed.

Other methods of providing tamper evidence are seen in FIGS. 16 and 17. A shrink wrap cover, though not considered adequate alone because of the general availability of shrink wrapping equipment, provides additional protection as seen in FIG. 16. It is preferable to provide a difficult-to-reproduce printed pattern on the shrink wrap to discourage tampering. An adhesively attached seal which can be applied and later peeled off, as is well known in the art, may also be used. Note that, in combination, inserted tabs 142 and tabs 47 securely lock container lid 22 to container 30 until outer wall 148 is removed. The removal of outer wall 148 substantially obviates reuse of collar 140.

Figure 18:
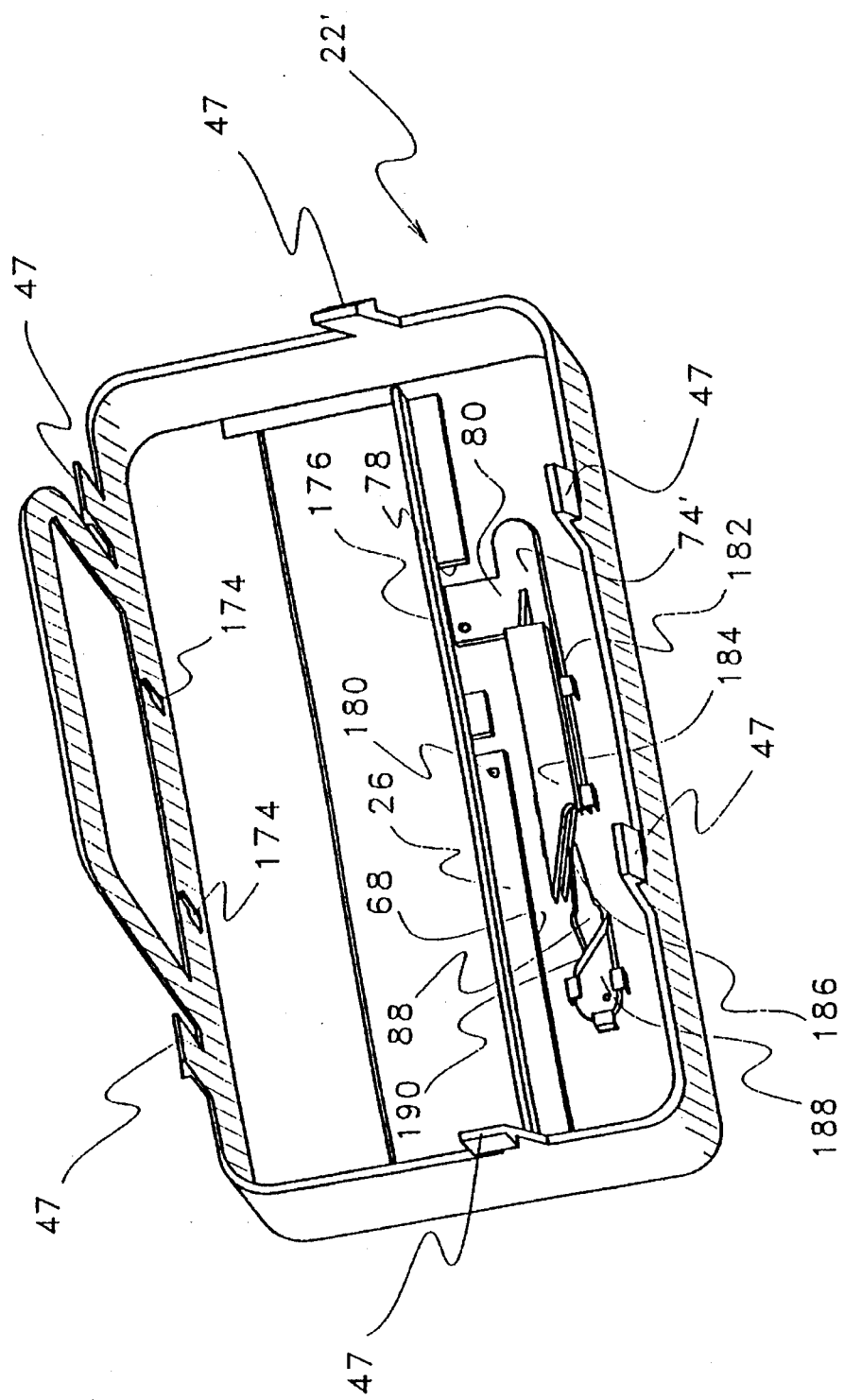
FIG. 18 is a perspective of an interior of a lid with a slider in position permitting the lid to open and permitting a tube cutting knife edge to be seen.
Figure 19:
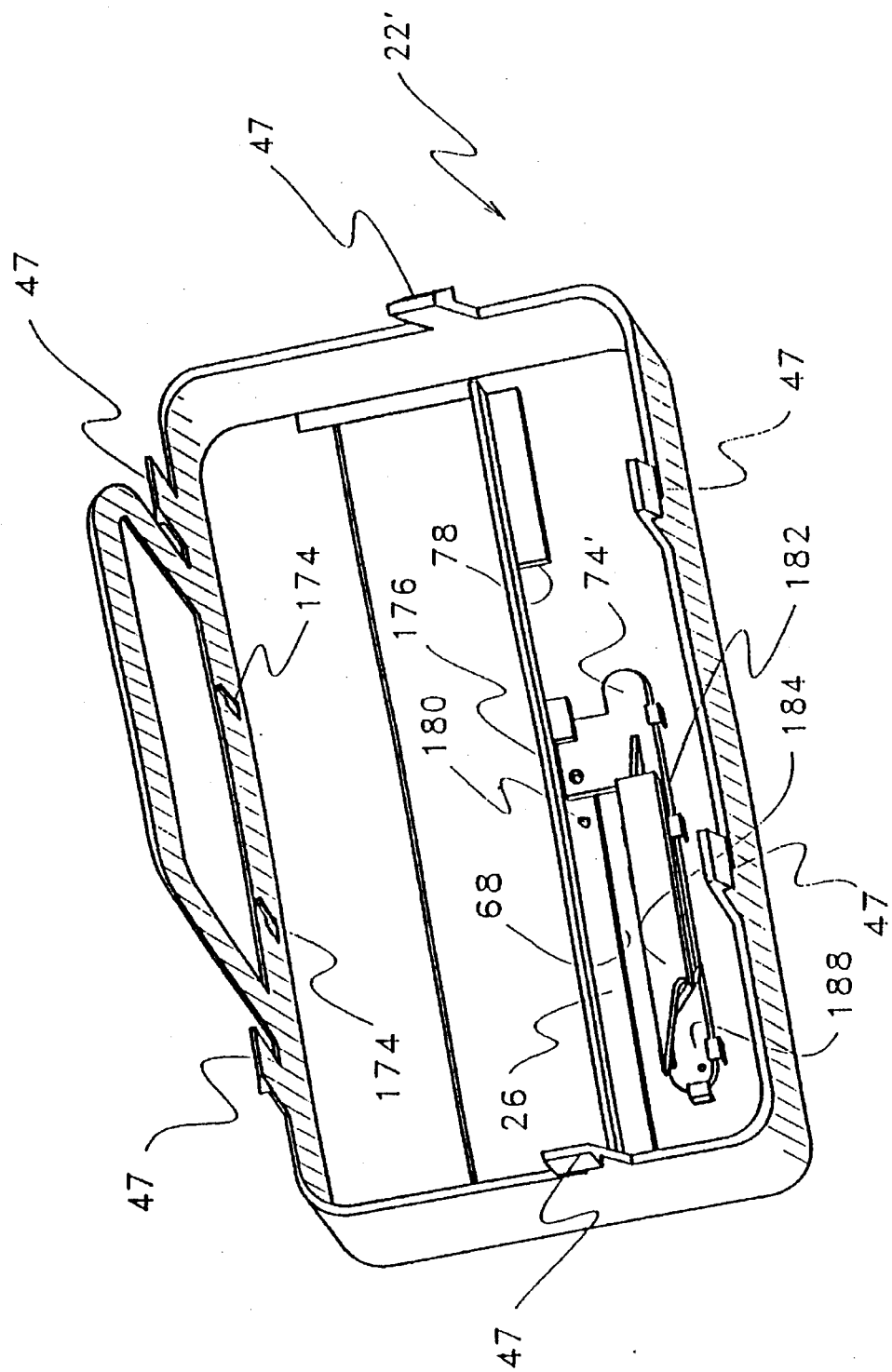
FIG. 19 is a perspective of the lid seen in FIG. 18 with the slider in a container closed position.
Figure 20:
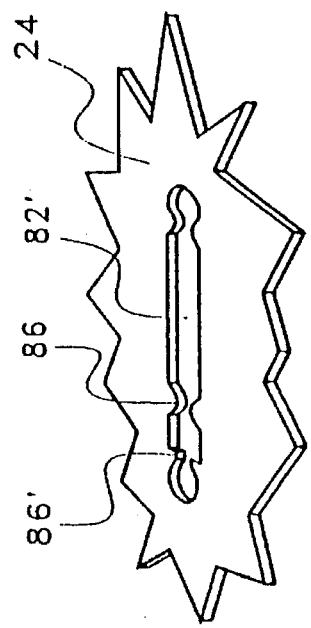
FIG. 20 is a perspective of a portion of a lid showing a slit through which a knob of the slider slides to open, closed and locked positions.

Attention is now drawn to FIGS. 18–20, wherein additional inventive elements of the invention are seen. In FIG. 18, a modified container lid body 22' is seen to comprise tabs 47, a pair of connecting guides 174 which aid in securing lid 22' to container body 30), handle 92 and other features which are similar to a container lid 22. Lid 22' (and lid 22) may also comprise a locking hole 176 disposed in tab 80' (or in tab 80).

In a presently preferred embodiment, an elongated slit 82' provides one extra step past close whereby container assembly is permanently locked by affixing biased flap 26 to tab 80' (or tab 80). Slit 82' is seen in FIG. 20. The extra step is permitted by an extension of slit 82' through a second neck section 86'. Actual locking is accomplished by pushing knob 84 to move tab 80 over a locking pin 180, seen in FIGS. 18 and 19. The action of pushing tab 80 over locking pin 180 should require enough increase in force over just moving knob through the necked sections to guard against inadvertent locking as such locking is permanent and excludes the container from future use. Note that the interlocking pans are unavailable to a user (i.e all interlocking pans are contained within the container and are inaccessible to tools which might be used to unlock or separate them.

An optional tube cutting feature is added to lid 22' as seen in FIGS. 18 and 19. To add the tube cutting feature, plate 74 is replaced by a two-layered slider 74'. Slider 74' comprises a superior layer 182 and an inferior layer 184. Superior layer 182 is substantially the same form as plate 74 except for a tube capturing curve on the closing end 186.

Disposed at an end of the tapered opening which is distal from end 186 is a sharpened blade 188. Blade 188 comprises a sharp knife edge 190 disposed proximally toward end 186 and is elevated such end 186 passes between knife edge 190 and lid 22'. Inferior layer 184 comprises an elongated form which is similar to the form of layer 182, but is separated a sufficient distance from layer 182 to permit blade 188 to pass therebetween. In this manner, a tube inserted into tapered opening 88 while slider 74' is in the position seen in FIG. 18 is severed by blade 188 when slider 74' is moved to the position seen in FIG. 19.

Figure 21:
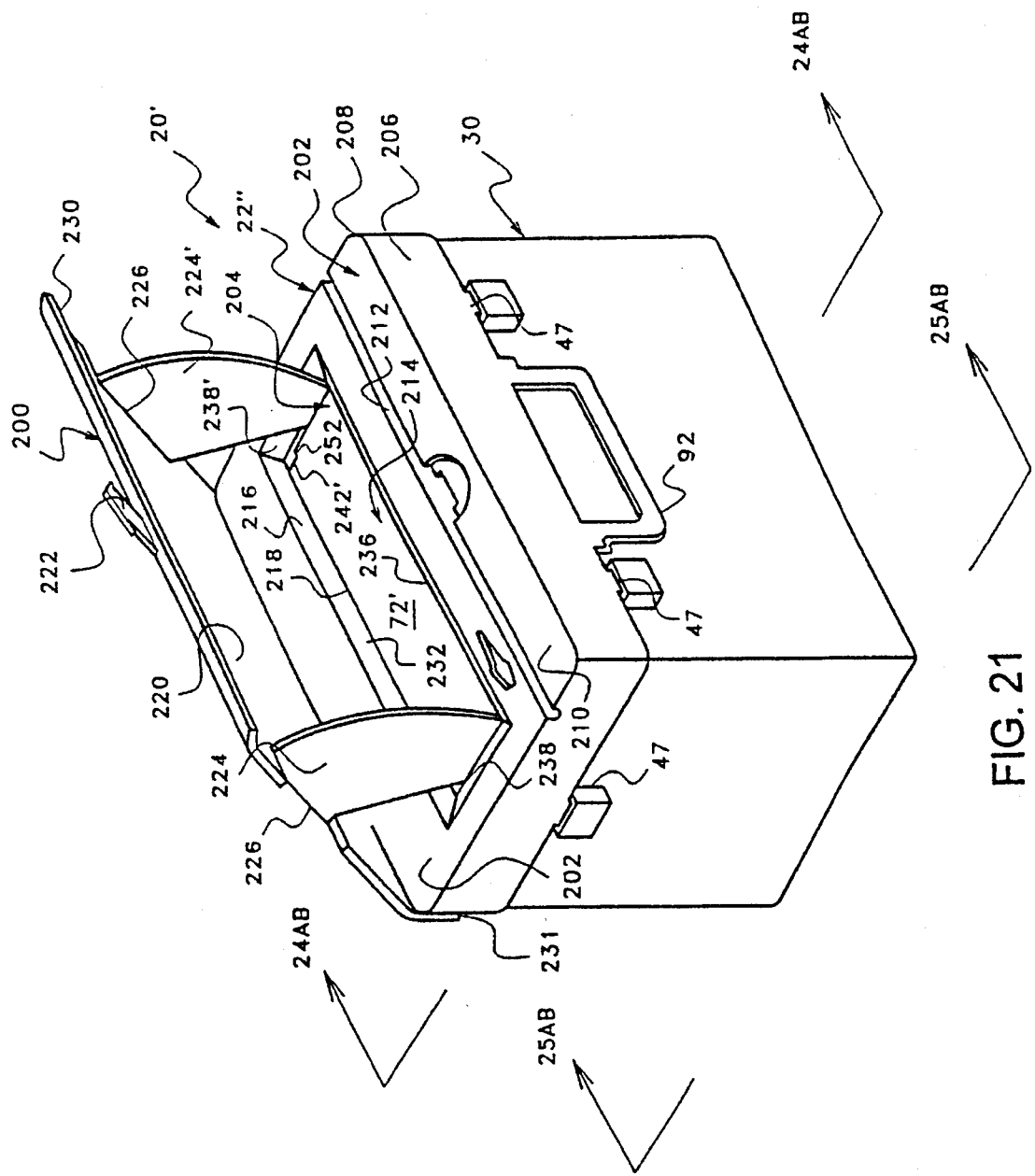
FIG. 21 is a perspective of a container having a lid body molded as a single part.

Reference is now made to FIG. 21 wherein a container assembly 20' embodiment of this instant invention is seen to comprise a unitarily molded lid body 22" and a permanently attachable container body 30. As container body 30 and related methods of affixing lids to body 30 is described earlier herein, no further description of either body 30 or modes of attachment is provided hereafter.

Even though it is an important financial consideration for lid body 22" to be made as a single injection molded part, for purposes of understanding the construction of lid body 22', it may be considered as being made up of a number of individual parts comprising a cover 200, a general top frame section 202 and a safety cradle 204. Top section 202 comprises a series of tabs which are similar in form and function to tabs 47, and are therefore referenced by tabs 47. When assembled to a container body 30, each tab 47 descends downward from a rim part 206 which is continuously and contiguously connected by a rounded peripheral edge 208 to a generally planar, horizontally disposed top portion 210. At the front of the container, a handle 92 is integrally molded to the top as earlier described for other lids which are within the scope of this invention. In combination, rim part 206, edge 208 and portion 210 comprise a slot 212 which is disposed parallel to that position of edge 206 which is associated with handle 92.

Portion 210 of section 202 further comprises an elongated rectangular hole 214 which provides access for depositing soiled parts upon safety cradle 204. Surrounding hole 214, section 202 comprises an elongated, vertically disposed extremity 216 which is defined at its lower limit by an edge 218. In use, edge 218 is normally horizontally disposed.

Figure 22:
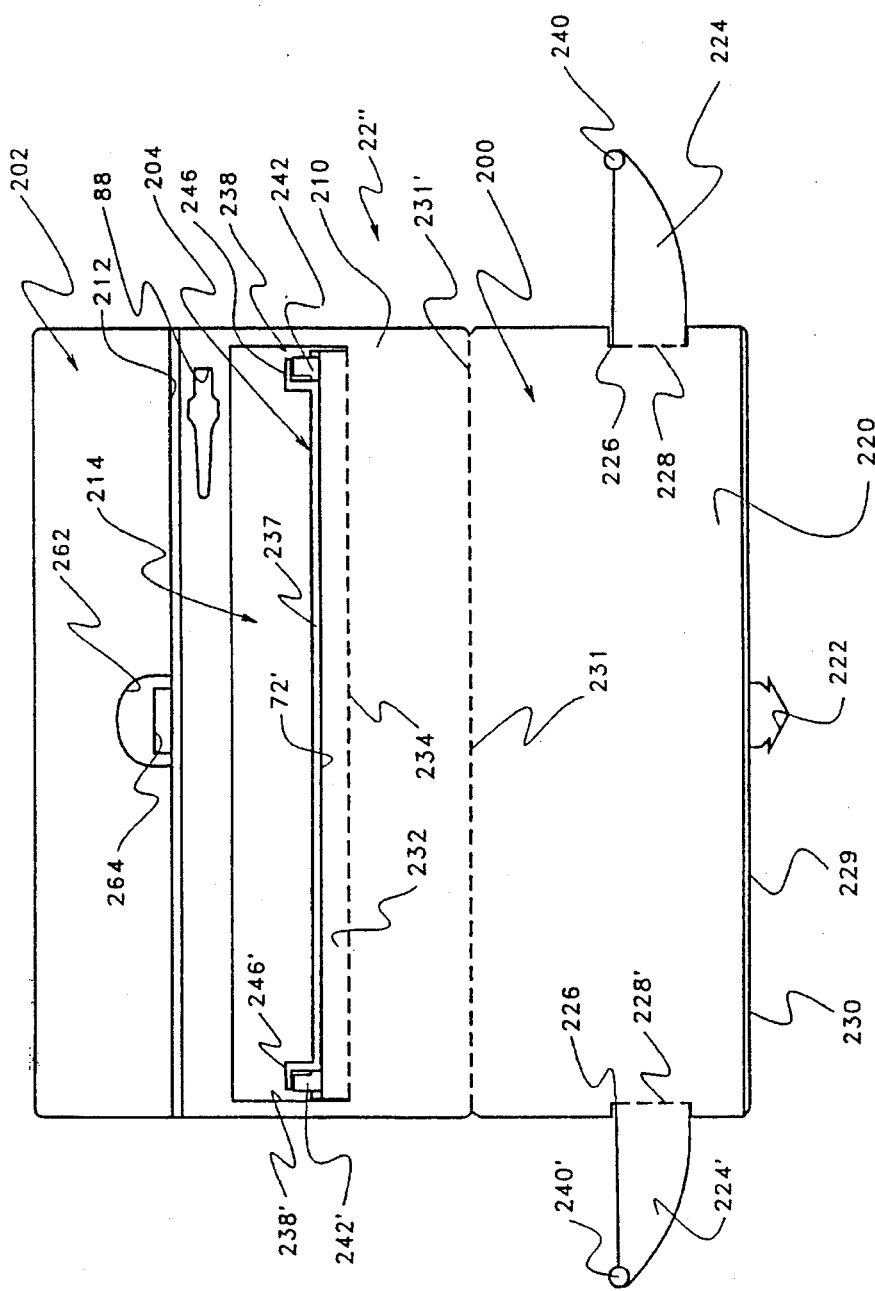
FIG. 22 is a top elevation of the lid body of FIG. 21 before being folded for assembly upon a container base.

Cover 200 comprises a substantially planar part 220, a lift tab 222, a pair of outwardly extending arms 224 and 224' and a pair of hinged connections, each numbered 226. As best seen in FIG. 22, cover 200 is integrally connected to top section 202. Arms 224 and 224' are bendably connected to part 220 along dashed lines 228 and 228', respectively, to form the hinged connections 226. Ventrally, planar part 220 is seen to connect to a medially disposed lift tab 222 along a line 229 of an upwardly distending insert edge 230.

The top elevation orientation of FIG. 22 shows lid body 22" molded as a single integral part and shows the combined part as a molded orientation of cover 200, section 202, and safety cradle 204. FIGS. 23–25B provide better cross sectional detail of some of the upwardly and downwardly distending (vertically oriented) parts of lid 22". Some parts, such as tabs 47 and handle 92, have been removed from FIGS. 24–25B for clarity of presentation.

Figure 24A:
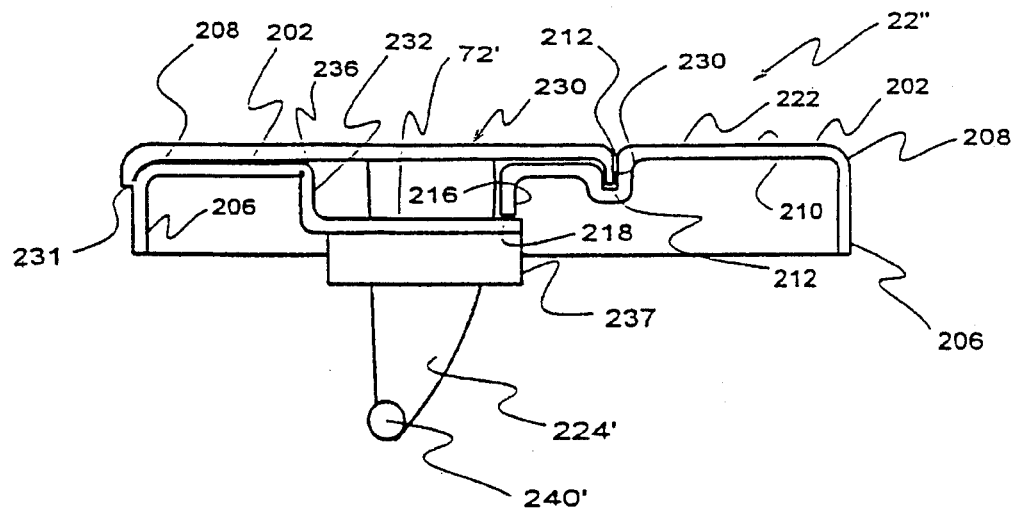
FIG. 24A is a cross section of the lid body of FIG. 21 taken along lines 24AB—24AB of FIG. 21, wherein a cover of the lid body is closed.
Figure 24B:
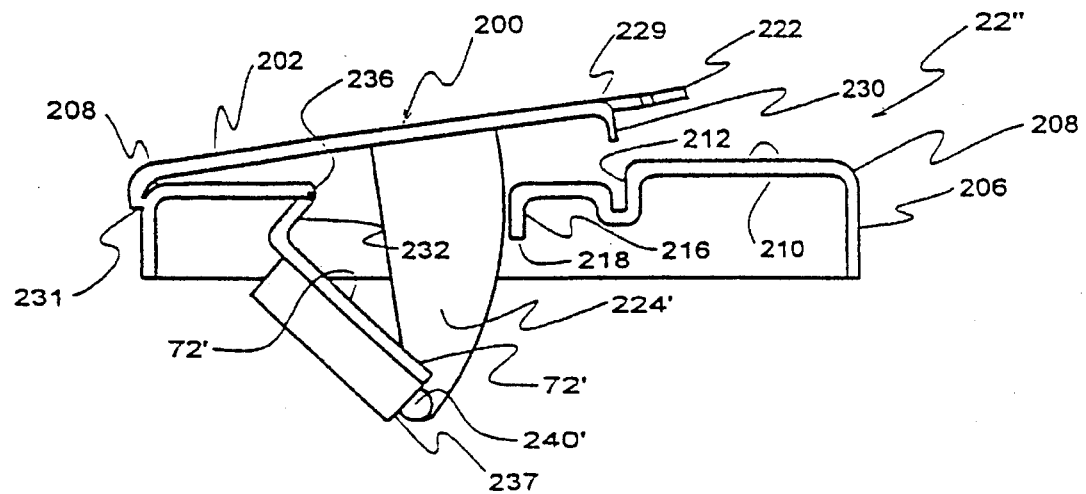
FIG. 24B is a cross section of the lid body of FIG. 21 taken along lines 24AB—24AB of FIG. 21, wherein a cover of the lid body is nearly closed.
Figure 25A:
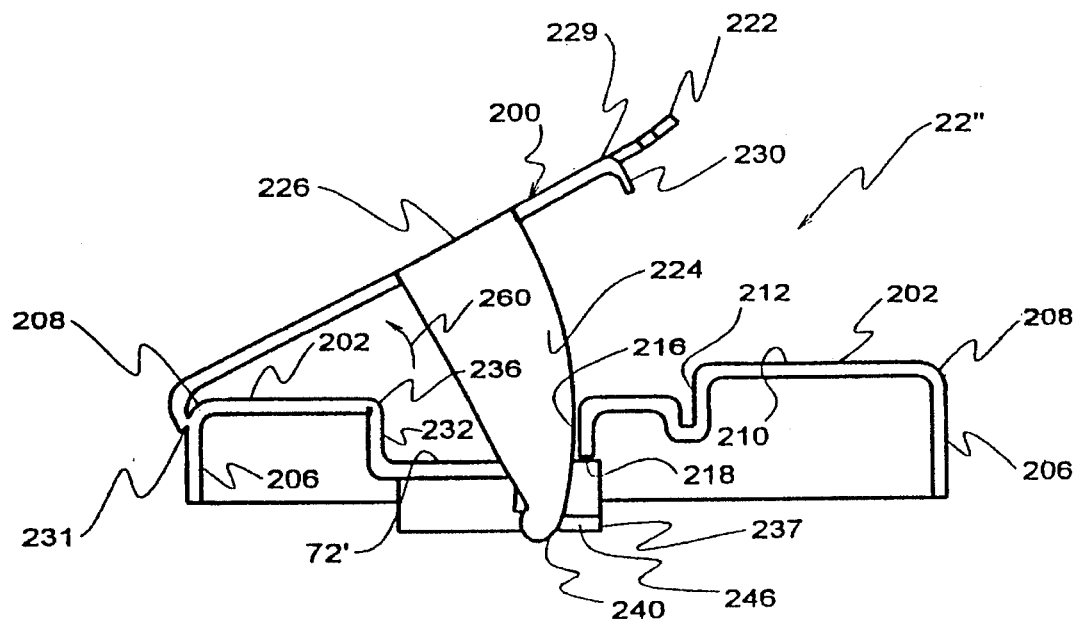
FIG. 25A is a cross section of the lid body of FIG. 21 taken along lines 25AB—25AB, wherein an arm portion of the cover is opened to near engagement with a safety cradle portion of the lid body.
Figure 25B:
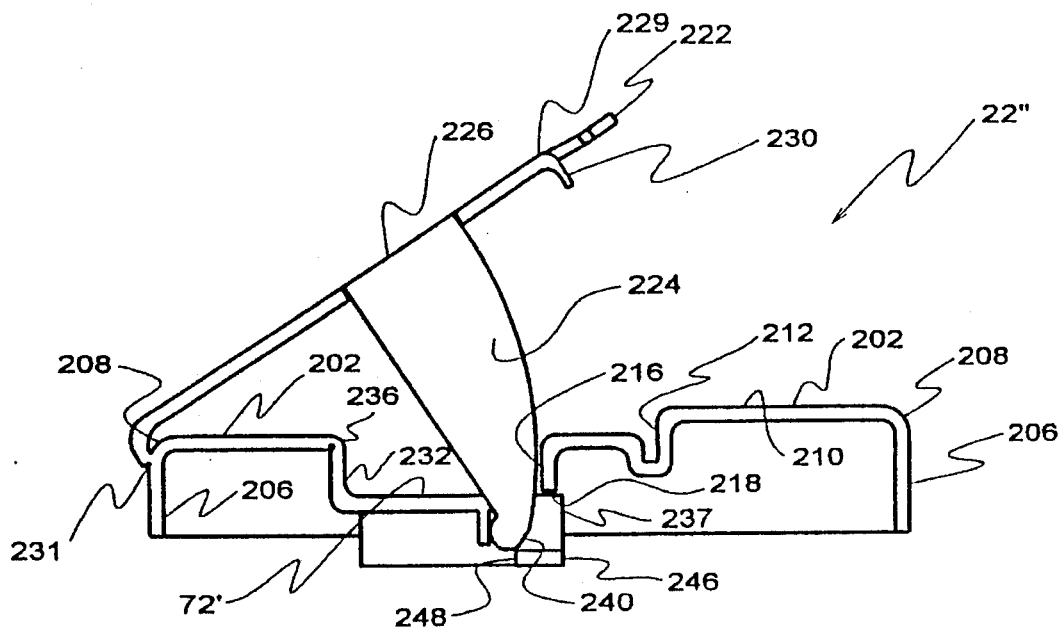
FIG. 25B is a cross section of the lid body of FIG. 21 taken along lines 25AB—25AB, wherein the same arm portion of the cover mentioned for FIG. 25A above is moved into engagement with the safety cradle portion of the lid body.

As best seen in FIGS. 24–25B, Safety cradle 204 comprises a floor 72' (normally disposed at a horizontal rest position) and a hinge member 232. Hinge member 232 is connected to section 202 along dashed line 234 to form a biased hinge 236. Molding procedures for making such biased hinges are well known in the plastics molding art. Referring again to FIG. 22, hinge member 232 is seen to be molded in substantially the same planar orientation as portion 210. Floor 72' is molded in nearly normal orientation relative to the plane of member 232 such that a leading edge 237 of floor 72' extends upwardly out of the plane of FIG. 22.

Immediately upon retrieval from injection molding, member 232 is bent at a right angle along dashed line 234 to recess floor 72' into hole 214 such that floor 72' is biased by memory of hinge 236 to be forcibly engaged against edge 218. This portion of floor 72' against edge 218 is best seen in FIG. 25A.

Preferably after so bending hinge member 232, arms 218 and 218' are bent upward from the plane of FIG. 22 at right angles, and then, cover 200 is bent to permit arms 218 and 218' to project into hole 214 along lateral sides 238 and 238', respectively, of hole 214. In this manner, a pair of sliders 240 and 240' are placed in position for capture by a portion of safety cradle 204. Form and function of sliders 240 and 240' are addressed in detail hereafter.

Figure 23:
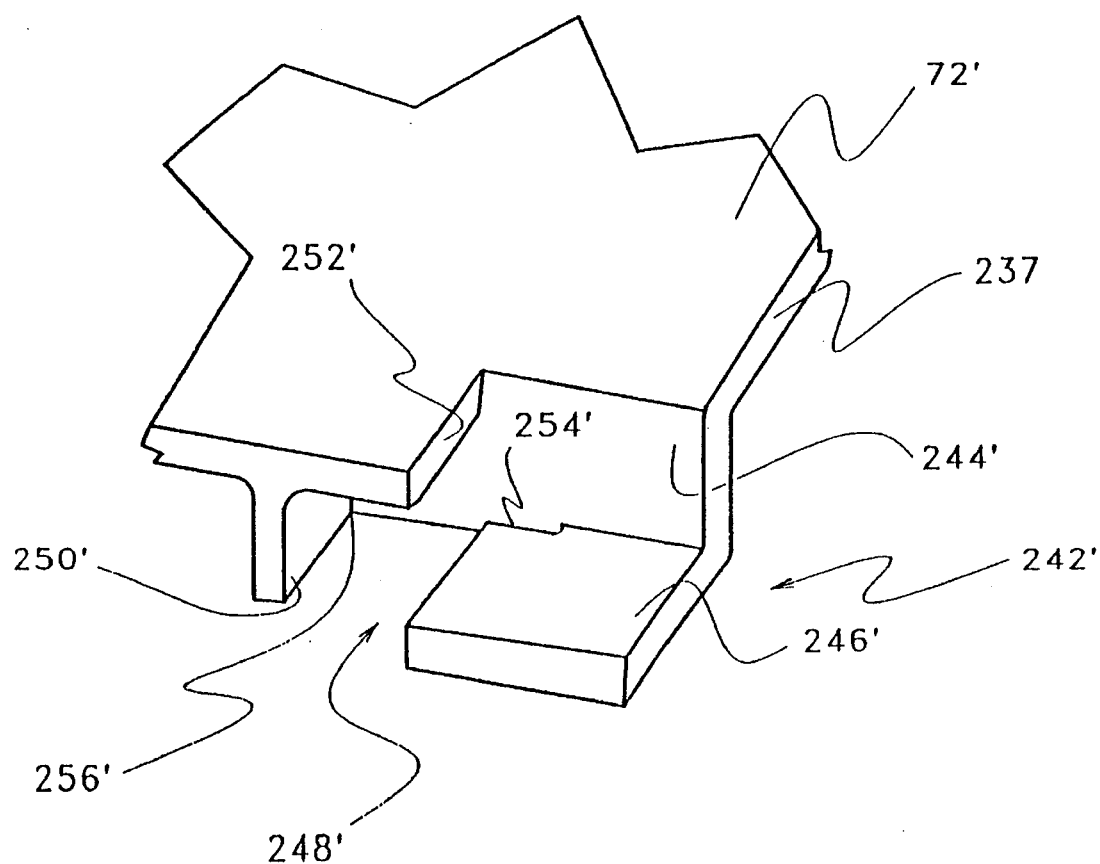
FIG. 23 is a perspective of a section of the lid body of FIG. 21.

Reference is now made to FIGS. 22 and 23 wherein a pair of structures 242 and 242', associated with operation of arms 224 and 224', respectively, are integrally molded as parts of safety cradle 204. Each structure 242 and 242' is disposed at a corner of safety cradle which is distally disposed away from hinge member 232. Structure 242 is a mirror image of structure 242'.

A perspective of structure 242' is seen in FIG. 23. Inferiorly disposed, after bending of hinge 232, is a vertical wall 244'. Distending outward from wall 244, generally toward side 238', is a slider forced, horizontally disposed tab 246'. Distending downward from floor 72' and separated by a space 248' away from tab 246' is a slider catching tab 250'. Safety cradle 204 also comprises a corner cut formed by wall 244' and an edge 252', orthogonally disposed relative to wall 244'. Edge 252' is disposed sufficiently close to edge 237 such that when floor 72' is biased against edge 218 there is not sufficient clearance for slider 240' to be raised out of capture by the combination of tab 250' and floor 72'.

Further, tabs 246' and 250' comprise a portion of each tab which is relieved from wall 244'. Such relief is seen as slot 254' between tab 246' and wall 244' and slot 256' between tab 250' and wall 244'. Referring once more to FIG. 22, sliders 240 and 240' preferably have a circular transverse face 258 and 258', respectively. Each slider 240 and 240' comprises an elongated shape, rising from arms 224 and 224', respectively, in the form of a cylinder. As such, when arms 224 and 224' are bent, as earlier described, sliders 240 and 240' are inwardly disposed relative to each structure 242 and 242'.

To move arms 224 and 224' and associated sliders 240 and 240' into position for use, after bending the arms as earlier described, cover 200 is rotated about hinge 231 in a direction which causes cover 200 to close against an associated area of portion 210 of section 202. The rotation of cover 200 is continued until sliders 240 and 240' contact floor 72'. To move cover 200 into a state where cover 200, and its sliders 240 and 240', are irreversibly caught and trapped by a combination of floor 72' and structures 242 and 242', cover 200 is compelled to force safety cradle 204 away from edge 218. Cover 200 is so moved until sliders 240 and 240' have entered into contact with tabs 246 and 246' and, thereafter, away from edge 237 and tabs 246 and 246' (as best seen in FIG. 24B. It is important to note that rotation of cover 200 about hinge 231 and related direction of travel of sliders 240 and 240' is eccentric relative to consequential rotation of safety cradle 204 about biased hinge 236. It is for this reason that each slider 240 and 240' tends to slide toward edge 237 as cover 200 is closed. As a result, each slider 240 and 240' ultimately slides free of structure 242 and 242', respectively, as cover 200 nears closure. Again, see FIG. 24B.

As seen in FIG. 24A, when cover 200 is closed and insert edge 230 is frictionally engaged into slot 212, sliders 240 and 240' are released from each structure 242 and 242' thus permitting biased hinge 236 to return safety cradle 204 to pressed engagement of floor 72' against edge 218. In this manner, biased hinge 236 is not unduly stressed while cover 200 is closed.

In normal operation, it is preferred that safety cradle 204 not be touched by a user when soiled medical trash is deposited into container assembly 20'. For this reason, it is preferred that opening of safety cradle only be activated remotely by closing of cover 200. In this manner, the contaminated area of cradle 204 is physically separated from the top of cover 200 where a users hands touch. By compelling cover 200 to travel in a closing direction cradle 204 is separated from edge 218 and thereby opened to deposit contents placed upon floor 72' into container body 30. Note that, if deposition of contents occurs before closure of cover 200 and therefore rotational pressure is removed therefrom, cover 200 is returned to an open orientation by force of bias hinge 236 when at least one slider 240 or 240' is captured by structure 242 or 242', respectively. If cover 200 is pushed to closure, sliders 240 and 240' are freed as earlier described at the point seen in FIG. 24B and cover 200 rests in the position seen if FIG. 24A.

Of course, each slider 240 and 240' must be recaptured into structures 242 and 242', respectively, before cover 200 can effectively be used to open cradle 204. Recapture of sliders 240 and 240' into containment by structures 242 and 242' is best seen in FIGS. 25A and 25B. Recapture is begun by rotating cover 200 in direction of arrow 260 until each slider is engaged in an entry space, such as space 248' of FIG. 23. Note tab flexibility defined for tabs 246' and 250' in FIG. 23. Such tab flexibility in structures 242 and 242' permits each slider 240 and 240' to enter into and become engaged in structures 242 and 242', respectively. Note also that compressive engagement of floor 72' against edge 218 stops floor 72' from further travel and resultingly causes displacement of structure 242 and 242' tabs to permit engagement and capture of sliders 240 and 240'. Once sliders 240 and 240' are engaged in structures 242 and 242', lid body 22" is ready to receive and dispose of soiled matter through cradle 204.

It is important to note that significantly more force may be used to capture sliders 240 and 240' in structures 242 and 242' than can be applied to cradle 204 when closing cover 200. Force which closes cover 200 tends to rotate cradle 204 and thereby moves each slider 240 and 240' toward a more stable and less releasible position across each tab 246 and 246', respectively. In this manner, sliders 240 and 240' enter into engagement via one route (i.e. spaces 248 and 248', respectively) and exit via another route (i.e. across edge 237).

It is also important to note that the top of lid body 22" is essentially flat when cover 200 is closed. As seen in FIG. 22, section 202 comprises a recess 262 wherein lift tab 222 resides when cover 200 is closed. Of course, tab 222 comprises sufficient resiliency to permit digitary access of tab 222 for purposes of freeing insert tab 230 from slot 212 and opening cover 200 to a ready position. Further tab, 222 comprises a shape (an arrow shape is seen in FIG. 21 ) which may be used to permanently lock lid body 22' (and therefore container 20') in a closed state. For this purpose, section 202 comprises a slot 264 within the area of recess 262 which irreversibly receives tab 222 when vertically inserted therein. As seen in FIG. 22, section 202 may also comprise one or more openings 88 for needle retraction. Each tapered opening is disposed at a position which permits protective enclosure by closure of cover 200.

In summary, the method and apparatus disclosed herein is a significant improvement from the present state of the containers for the sealed transport and disposal of medical instruments.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A container for use in transport and disposal of medical instruments, comprising:

a container body having an opening and an internal volume;

a self-closing biased flap at an associated ingress site superiorly disposed as a part of the container to provide for selective deposit of used medical instruments into the volume, said flap being securely connected to the container body as part of a covering for the opening; and a safety guard disposed within the internal volume which denies a direct pathway through the ingress site to medical instruments and waste disposed within the volume, said safety guard comprising an access hole through which medical products having a size which permits ingress through the alternate ingress aperture are passed into the internal volume.

2. A container for use in transport and disposal of medical instruments, comprising:

a container body having an opening and an internal volume;

a self-closing biased flap at an associated ingress site superiorly disposed as a part of the container to provide for selective deposit of used medical instruments into the volume, said flap being securely connected to the container body as part of a covering for the opening; and a safety guard disposed within the internal volume which denies a direct pathway through the ingress site to medical instruments and waste disposed within the volume, said safety guard comprising a first acute angle relative to the plane of the self-closing biased flap and substantially comprises only sufficient material strength to support its own weight and therefore yields under weight of an item introduced through the opening to bend to a second angle which is less acute relative to the plane of the flap and therefore to a horizontal plane.

3. A method of transporting and storing and gaining access to unused medical materials by means of a container assembly comprising a lid body having an opening, a self-closing biased flap connected to the lid body for covering the opening, tamper evidence producing means for temporarily attaching the lid over an opening of an associated container, and a cradling means for insertion of medical materials into the container body through the opening, said cradling means having a floor disposed on the biased flap, comprising the steps of:

a) placing unused medical materials inside the container body; and b) using the tamper evidence producing means to temporarily secure the lid body over the container opening; and c) gaining access to the unused medical materials by substantially irreversibly displacing at least a portion of the evidence producing means thereby providing tamper evidence.

4. The method as defined in claim 3, wherein the using step comprises interposing the tamper evidence producing means between lid parts and associated container body parts which would otherwise be used to permanently interconnect the lid to the container body and interconnecting the lid to the container body by connecting the tamper evidence producing means to at least one lid part and at least one container body part.

5. The method as defined in claim 3 wherein the using step comprises inserting tab members of the lid into slots disposed in the tamper evidence producing means and inserting tab members of the tamper evidence producing means into slots disposed in the container body.

6. The method as defined in claim 3 wherein the gaining step comprises franging at least one part of the tamper evidence producing means.

7. The method as defined in claim 3 wherein the using step comprises at least partially enclosing the container assembly in a shrink wrap.

8. A container apparatus for use in transport and disposal of medical instruments, comprising:

a container body having an opening and an internal volume;

a lid which comprises means for permanently being affixed to the container body in a first orientation and for releasably attaching to the container body in a second orientation, said lid comprising means for selectively providing access through the lid to the opening; and a tamper evidence producing device which securely interconnects the container body to the lid in the second orientation and provides a release of the lid from the container body by manual action which produces irreversible structural change to the tamper evidence producing device.

9. The container apparatus as defined in claim 8 wherein the tamper evidence producing device comprises frangible parts which are structurally changed for release of the lid from the container body.

10. The container apparatus as defined in claim 8 further comprising a safety guard.

11. A method of disposing of used medical materials by means of a container assembly comprising a lid body having an opening, a self-closing biased flap connected to the lid body for covering the opening, means for permanently attaching the lid body over an opening of an associated container, means for permanently locking the biased flap closed, and a cradling means for insertion of medical materials into the container body through the opening, said cradling means having a floor disposed on the biased flap, comprising the steps of:

a) permanently securing the lid body to the associated container;

b) placing the used medical materials onto the floor of the cradling means;

c) pushing downward against the biased flap in an area adjacent to the cradling means, thereby allowing the used medical materials to fall inside the container assembly without operator contact; and d) when the container is filled to a desired level, closing and locking the biased flap closed.

12. A method of using a transport and disposal container assembly combination comprising the steps of:

a) providing a container body having an accessible opening; a lid body having a normally closed ingress site, a self-closing biased flap connected to the lid body for selectively covering and thereby closing the ingress site and for intermittent access to the opening at the site; a lock associated with the lid for permanently locking the ingress site closed; tamper evidence producing means for temporarily attaching the lid over the opening of the container; and a cradling means for insertion of medical materials into the container body at the ingress site, said cradling means having a floor disposed on the biased flap;

b) placing unused medical materials inside the container body;

c) using the tamper evidence producing means to temporarily secure the lid body over the container opening;

d) at a user site, noting whether or not the tamper evidence producing means shows evidence of tampering;

e) if there is evidence of tampering, taking appropriate responsive action to a container assembly combination which shows evidence of tampering;

f) if there is no evidence of tampering, gaining access to the unused medical materials by substantially irreversibly displacing at least a portion of the tamper evidence producing means;

g) removing the unused medical materials;

h) permanently affixing the lid to the container body to form the combination for use as a medical waste disposal container; depositing used medical materials through the ingress site; and j) when the medical waste disposal container is filled to a desired level, locking the lid closed at the ingress site to preclude any further filling.

13. A lid for a container apparatus for medical sharps and associated waste comprising:

an ingress site normally closed by a biased flap;

a tapered hole which permits direct insertion of medical needles and other tubing connected devices through the lid;

slider means providing manual positioning to at least three positions comprising:

an open position whereat the biased flap may be selectively opened and medical needles and other tubing connected devices may be delivered through the tapered hole;

a closed position whereat the biased flap is maintained in a closed position and the tapered hole is covered; and a locked position whereat the biased flap and tapered hole are permanently closed to further access.

14. A lid for a container apparatus for medical sharps and associated waste comprising:

an ingress site normally closed by a biased flap;

a tapered hole which permits direct insertion of medical needles and other tubing connected devices through the lid;

slider means providing manual positioning to at least three positions comprising:

an open position whereat the biased flap may be selectively opened and medical needles and other tubing connected devices may be delivered through the tapered hole;

a closed position whereat the biased flap is maintained in a closed position and the tapered hole is covered;

a locked position whereat the biased flap and tapered hole are permanently closed to further access; and the lid further comprising a tube cutter disposed at the tapered hole and activated by the slider.

15. A method of transporting and storing unused medical materials from a point of assembly to a point of usage within a self-contained shipping container assembly and then using the same container assembly as a secure sharps container thereafter, comprising the steps of:

a) providing, as a bottom portion of the container, a container body having a bottom and a plurality of sides defining a preselected volume for storing prescribed quantity of the unused medical materials, said sides having a top portion that defines a container body opening;

b) providing a lid for releasibly closing off said container body opening during said storing and transporting, said lid being selectably removable from a temporarily attached position with respect to said container body opening so as to permit the bulk removal of all of said preselected quantity of unused medical materials;

c) providing a means for reclosing said container including said lid and additional locking means for irreversibly securing said lid to said container body opening;

d) providing a means for selectively disposing sharps into the container body after the lid is securely disposed upon the container body;

e) placing unused medical materials inside the container body;

f) temporarily securing the lid over the container body opening to close said opening and to form a self-contained shipping container in which said bottom, sides and lid enclose said unused medical materials in said shipping container;

g) transporting the so-filled shipping container to a site where the materials are to be used;

h) displacing the lid relative to the container body opening for access to the materials;

i) replacing the lid such that the lid is irreversibly secured to the container body, thereby forming a sharps container;

j) disposing used sharps and other biohazard materials into the sharps container for safe keeping.

16. The method as defined in claim 15, wherein the temporarily securing step comprises disposing the lid over the container body such that tabs and slots, which are specifically aligned to irreversibly secure the lid to the container body, are misaligned for temporary securement of the lid body to the container for transport and later removal of new medical materials.

17. A method as defined in claim 15 comprising a further step of permanently locking the container closed, when filled to a predetermined level, to exclude further disposing of used sharps into a full container thereby creating a hazardous condition of an overfilled container.

18. A method of disposing of used medical materials by means of a container assembly comprising a lid body having an opening, a self-closing biased flap connected to the lid body for covering the opening, means for permanently attaching the lid body over an opening of an associated container, a cradling means for insertion of medical materials into the container body through the opening, said cradling means having a floor disposed on the biased flap, and a hinged cover having a releasable latch which is selectively closed and releasably latched to deny access to the cradling means, said method comprising the steps of:

a) permanently securing the lid body to the associated container;

b) placing the used medical materials onto the floor of the cradling means;

c) pushing downwardly against the biased flap in an area adjacent to the cradling means, thereby allowing the used medical materials to fall inside the container assembly without operator contact; and d) closing the cover and engaging the releasable latch, thereby restricting access to the cradling means until the cover is purposefully opened.

19. The method as defined in claim 18, wherein the securing step comprises disposing the lid body over the container opening and inserting a plurality of tabs secured to the lid body into a corresponding female slot located on the container body such that protruding tab-edges lock the tabs in place.

20. A method as defined in claim 18, wherein the securing step comprises interlocking a plurality of hinged pull tabs secured to the lid body, each tab including a distal end at which is disposed a female end of an arrow lock, with a corresponding male end located on the container for each female end disposed on the lid body.

21. A container apparatus for use in disposal of medical instruments, comprising:

a container body having an opening and an internal volume;

a lid for said container apparatus comprising means for permanently attaching the lid to said container and which is molded as a single part, said lid comprising:

a frame section comprising the attaching means;

a safety cradle section disposed within the bounds of the frame section which comprises a biased hinge attachment to the frame section, the bias of the hinge maintaining the safety cradle in a normally closed position; and a cover section, hingedly affixed to the frame section, which, in a closed position, covers and protects the safety cradle and which comprises at least one actuator which when moved into operative engagement of the safety cradle operates to open the safety cradle in opposition to the bias of the hinge as the cover is being closed and which disengages from the safety cradle when the cover is closed, thereby permitting the biased hinge of the safety cradle to return to the normally closed position without actuator opposition.

22. A container apparatus according to claim 21 wherein the at least one actuator comprises means for opening the safety cradle section and the safety cradle section comprises means for releasibly engaging the actuating means such that the at least one actuator is engaged in a first rotational position of the cradle section and is released from engagement in a second rotational position of the cradle section.

23. A container apparatus according to claim 21 wherein the cover section comprises a tab for manually raising the cover.

24. A container apparatus according to claim 23 wherein the frame section comprises a slot and the tab comprises an interlocking shape whereby the cover is permanently locked when the tab is inserted to the slot, thereby thwarting attempts into further access to the container.

25. A container apparatus according to claim 21 wherein, in combination, the cover section and the frame section comprise means for releasibly securing closure of the cover section to the frame section when the cover is closed.

26. A container apparatus according to claim 21 wherein the cover comprises a living hinge which is integrally attached by molding to the frame section.

27. A container apparatus according to claim 21 wherein the safety cradle comprises a biased hinge which is integrally affixed by molding to the frame section.

28. A container apparatus according to claim 21 wherein the at least one actuator comprises an arm which is bent from the plane of the cover after molding.

29. A container apparatus according to claim 21 wherein the actuator comprises at least one slider for engagement with the safety cradle.

30. A container apparatus according to claim 21 wherein the slider comprises a cylindrical shape.

31. A container apparatus according to claim 21 wherein the frame section comprises a rim disposed about the periphery of the lid.

32. A lid body for use in disposal of medical instruments, comprising means for permanently attaching the lid body to a container for use as a container assembly used in disposal of medical sharps and other waste, said lid being molded as a single part comprising:

a frame section comprising the attaching means;

a safety cradle section disposed within the bounds of the frame section which comprises a biased hinge attachment to the frame section, the bias of the hinge maintaining the safety cradle in a normally closed position; and a cover section, hingedly affixed to the frame section, which, in a closed position, covers and protects the safety cradle and which comprises at least one actuator which when moved into operative engagement of the safety cradle operates to open the safety cradle in opposition to bias of the hinge as the cover is being closed and which disengages from the safety cradle when the cover is closed, thereby permitting the biased hinge of the safety cradle to return to the normally closed position without actuator opposition.

33. A lid body according to claim 32 wherein the at least one actuator comprises means for opening the safety cradle section and the safety cradle section comprises means for releasibly engaging the actuating means such that the at least one actuator is engaged in a first rotational position of the cradle section and is released from engagement in a second rotational position of the cradle section.

34. A lid body according to claim 32 wherein the cover section comprises a tab for manually raising the cover.

35. A lid body according to claim 34 wherein the frame section comprises a slot and the tab comprises an interlocking shape whereby the cover is permanently locked by inserting the tab into the slot, thereby thwarting attempts for further access to the container.

36. A lid body according to claim 32 wherein, in combination, the cover section and the frame section comprise means for releasibly securing closure of the cover section to the frame section when the cover is closed.

37. A lid body according to claim 32 wherein the cover comprises a living hinge which is integrally attached by molding to the frame section.

38. A lid body according to claim 32 wherein the safety cradle comprises a biased hinge which is integrally affixed by molding to the frame section.

39. A lid body according to claim 32 wherein the at least one actuator comprises an arm which is bent from the plane of the cover after molding.

40. A lid body according to claim 32 wherein the actuator comprises at least one slider for engagement with the safety cradle.

41. A lid body according to claim 32 wherein the slider comprises a cylindrical shape.

42. A lid body according to claim 32 wherein the frame section comprises a rim disposed about the periphery of the lid.

43. A method for making a lid for use with a container for medical sharps and other medical waste comprising the steps of:

molding the lid as a single part comprising a frame section comprising means for attaching the lid to the container;

a safety cradle section disposed within the bounds of the frame section which comprises a biased hinge attachment to the frame section, the bias of the hinge maintaining the safety cradle in a normally closed position; and a cover section, hingedly attached to the frame section, which, in a closed position, covers and protects the safety cradle and which comprises at least one actuator which when moved into operative engagement of the safety cradle operates to open the safety cradle in opposition to bias of the hinge as the cover is being closed and which disengages from the safety cradle when the cover is closed, thereby permitting the biased hinge of the safety cradle to return to the normally closed position without actuator opposition;

folding the biased hinge into biased engagement with the frame section;

folding the at least one actuator to an angle which permits operative engagement with the safety cradle; and closing the lid.

44. A method of transporting or disposing of medical materials by means of a container assembly comprising a lid body having an opening, a self-closing biased flap connected to the lid body for covering the opening, means in a first used position capable of temporarily attaching the lid over an opening of an associated container and in a second used position capable of permanently attaching the lid over the opening of the associated container, and a cradling means for insertion of medical materials into the container body through the opening, said cradling means having a floor disposed on the biased flap, comprising the steps of:

a) placing unused medical materials inside the container body when transporting medical materials;

b) temporarily securing the lid body over the container opening when transporting medical materials;

c) permanently securing the lid body to the associated container when disposing of medical materials;

d) placing the used medical materials onto the floor of the cradling means when disposing of medical materials; and e) pushing downward against the biased flap in an area adjacent to the cradling means, thereby causing the used medical materials to fall inside the container assembly without operator contact when disposing of medical materials.

45. The method as defined in claim 44, further comprising a step of changing from a position of temporarily securing the lid body to the container to a position of permanently securing the lid body to the container by rotating the lid one-hundred and eighty degrees.

46. A self-contained shipping and sharps container for transporting unused medical products after product manufacture to a point of product usage (whereat all such unused products are removed from said container), said container then being usable for safe storage of used sharp medical instruments, said container comprising:

a) a container body having a bottom and a plurality of sides integral with said bottom and sides defining a preselected volume having an opening for storing of a prescribed quantity of unused medical products;

b) a lid body comprising at least one biased opening covering flap, said lid body releasibly closing off said container body during said storage and having a first relative configuration of said lid body being selectably movable with respect to said container so as to permit the bulk removal of all of said preselected quantity of unused medical products;

c) means for reclosing said container including said lid body, said lid body having a second relative configuration wherein an additional locking means irreversibly secures said lid body to said container body when rotated about an axis transverse to a plane of said opening and with respect to said first relative configuration; and d) means for serially disposing of the used sharp medical instruments and other medical waste into said closed container having said lid body irreversibly secured to said container body.

47. A self-contained container according to claim 46 wherein said disposing means comprise cradling means, integrally attached to said lid body, by which used sharp medical instruments are serially disposed into said container.

48. A self-contained container according to claim 46 wherein said lid body comprises but a single, integral molded part.

49. A self-contained container according to claim 46 further comprising means for producing tamper evidence when said lid body is separated from said container body at the point of product usage.

50. A self-contained container according to claim 46 wherein said lid body comprises means for fully detaching said lid body from container body for removal of said unused medical products.

51. A self-contained container according to claim 46 wherein said lid body comprises at least one biased flap.

* * * * *